United States Patent
Tomioka et al.

(10) Patent No.: US 12,207,542 B2
(45) Date of Patent: Jan. 21, 2025

(54) METHOD FOR MANUFACTURING PHOTOELECTRIC CONVERSION ELEMENT AND OPTICAL SENSOR

(71) Applicant: Japan Display Inc., Tokyo (JP)

(72) Inventors: Yasushi Tomioka, Minato-ku (JP); Akio Takimoto, Minato-ku (JP)

(73) Assignee: Japan Display Inc., Tokyo (JP)

( * ) Notice: Subject to any disclaimer, the term of this patent is extended or adjusted under 35 U.S.C. 154(b) by 410 days.

(21) Appl. No.: 17/655,448

(22) Filed: Mar. 18, 2022

(65) Prior Publication Data

US 2022/0320440 A1 Oct. 6, 2022

(30) Foreign Application Priority Data

Mar. 30, 2021 (JP) .................. 2021-058790

(51) Int. Cl.
  *H01L 51/00* (2006.01)
  *G06F 3/042* (2006.01)
  *H10K 30/87* (2023.01)
  *H10K 85/10* (2023.01)

(52) U.S. Cl.
  CPC .......... *H10K 85/111* (2023.02); *G06F 3/0421* (2013.01); *H10K 30/87* (2023.02)

(58) Field of Classification Search
  CPC ................................................. H10K 85/111
  See application file for complete search history.

(56) References Cited

U.S. PATENT DOCUMENTS

| 4,716,216 A | * | 12/1987 | Takekoshi | .......... | C08G 73/1064 |
| | | | | | 528/229 |
| 5,331,182 A | | 7/1994 | Takimoto et al. | | |
| 5,486,442 A | * | 1/1996 | Takimoto | ............... | C08G 69/40 |
| | | | | | 349/114 |

OTHER PUBLICATIONS

Office Action issued on Jun. 6, 2024, in corresponding German Application No. 10 2022 203 024.9, 14 pages.
Takimoto, A. et al. "Electrophotographic and structural studies on novel photoconductive polyimide films", Journal of Applied Physics, vol. 70, No. 5, p. 2799. (1991) 8 pages.

* cited by examiner

*Primary Examiner* — Nathan T Leong
(74) *Attorney, Agent, or Firm* — Maier & Maier, PLLC

(57) ABSTRACT

A method for manufacturing a photoelectric conversion element according to an aspect includes an active layer forming step of forming an active layer having a repeating unit represented by Chemical Formula 1. The active layer forming step includes: a first layer forming step of forming a first layer by applying polyamic acid serving as a precursor; a first heating step of heating the first layer at 120° C. for 20 minutes to 60 minutes; and a second heating step of heating the first layer at 230° C. to 280° C. for 10 minutes.

6 Claims, 20 Drawing Sheets

METHOD FOR MANUFACTURING PHOTOELECTRIC CONVERSION ELEMENT AND OPTICAL SENSOR

CROSS-REFERENCE TO RELATED APPLICATION

This application claims the benefit of priority from Japanese Patent Application No. 2021-058790 filed on Mar. 30, 2021, the entire contents of which are incorporated herein by reference.

BACKGROUND

1. Technical Field

What is disclosed herein relates to a method for manufacturing a photoelectric conversion element and to an optical sensor.

2. Description of the Related Art

An optical sensor includes a photoelectric conversion element such as a photodiode. The photoelectric conversion element disclosed in Non Patent Literature 1 has an active layer (polyimide layer) manufactured from polyimide. In addition, "Electrophotographic and structural studies on novel photoconductive polyimide films", Journal of Applied Physics, 1991, Vol. 70, No. 5, p. 2799 written by Akio Takimoto et al. (hereinafter, referred to as Akio Takimoto et al.) discloses that polyamic acid serving as a precursor of polyimide is heat-treated at 300° C. for 2 hours in order to produce an active layer (polyimide layer) in which the polyimide crystallizes and exhibits a photoelectric effect.

The active layer obtained by Akio Takimoto et al. has low sensitivity of the photoelectric effect.

For the foregoing reasons, there is a need for a method for manufacturing a photoelectric conversion element that has high sensitivity of the photoelectric effect of the active layer. There is also need for an optical sensor provided with a photoelectric conversion element that has high sensitivity of the photoelectric effect of the active layer.

SUMMARY

A method for manufacturing a photoelectric conversion element according to a first aspect of the present disclosure includes an active layer forming step of forming an active layer having a repeating unit represented by Chemical Formula 1 below. The active layer forming step includes: a first layer forming step of forming a first layer by applying polyamic acid serving as a precursor; a first heating step of heating the first layer at 120° C. for 20 minutes to 60 minutes; and a second heating step of heating the first layer at 230° C. to 280° C. for 10 minutes.

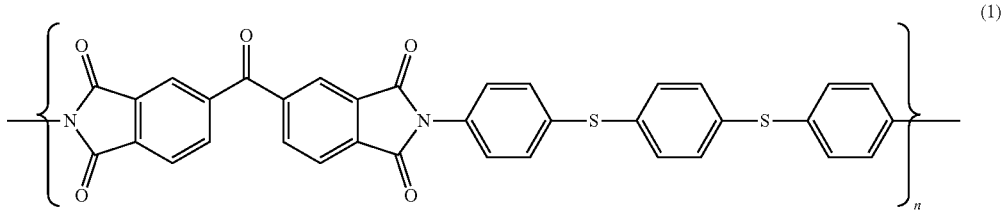

(1)

A method for manufacturing a photoelectric conversion element according to a second aspect of the present disclosure includes an active layer forming step of forming an active layer having a repeating unit represented by Chemical Formula 2 below. The active layer forming step includes: a first layer forming step of forming a first layer by applying a polyamic acid solution serving as a precursor of Chemical Formula 2 below; a first heating step of heating the first layer at 120° C. for 20 minutes to 60 minutes; and a second heating step of heating the first layer at 180° C. to 280° C. for 10 minutes.

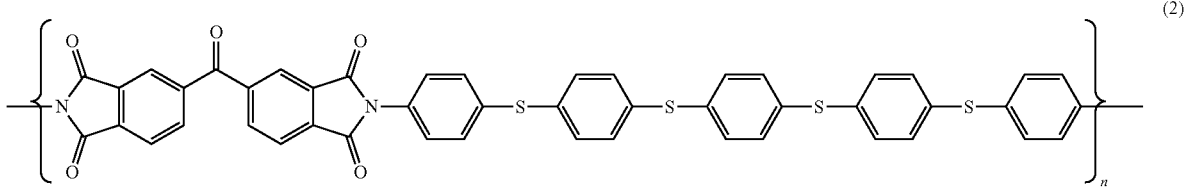

(2)

A method for manufacturing a photoelectric conversion element according to a third aspect of the present disclosure includes an active layer forming step of forming an active layer having a repeating unit represented by Chemical Formula 3 below. The active layer forming step includes: a first layer forming step of forming a first layer by applying polyamide acid that serves as a precursor and has a repeating unit represented by Chemical Formula 4 below; a first heating step of heating the first layer at 120° C. for 20 minutes to 60 minutes; and a second heating step of heating the first layer at 180° C. to 280° C. for 10 minutes.

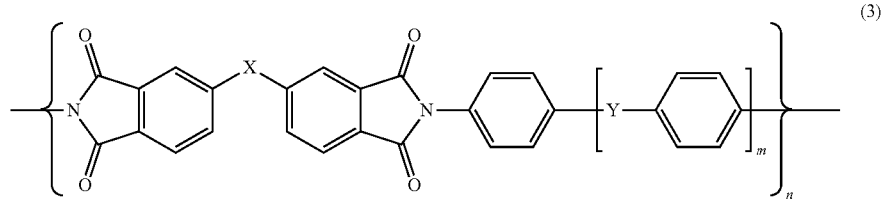

(3)

Figure 2:
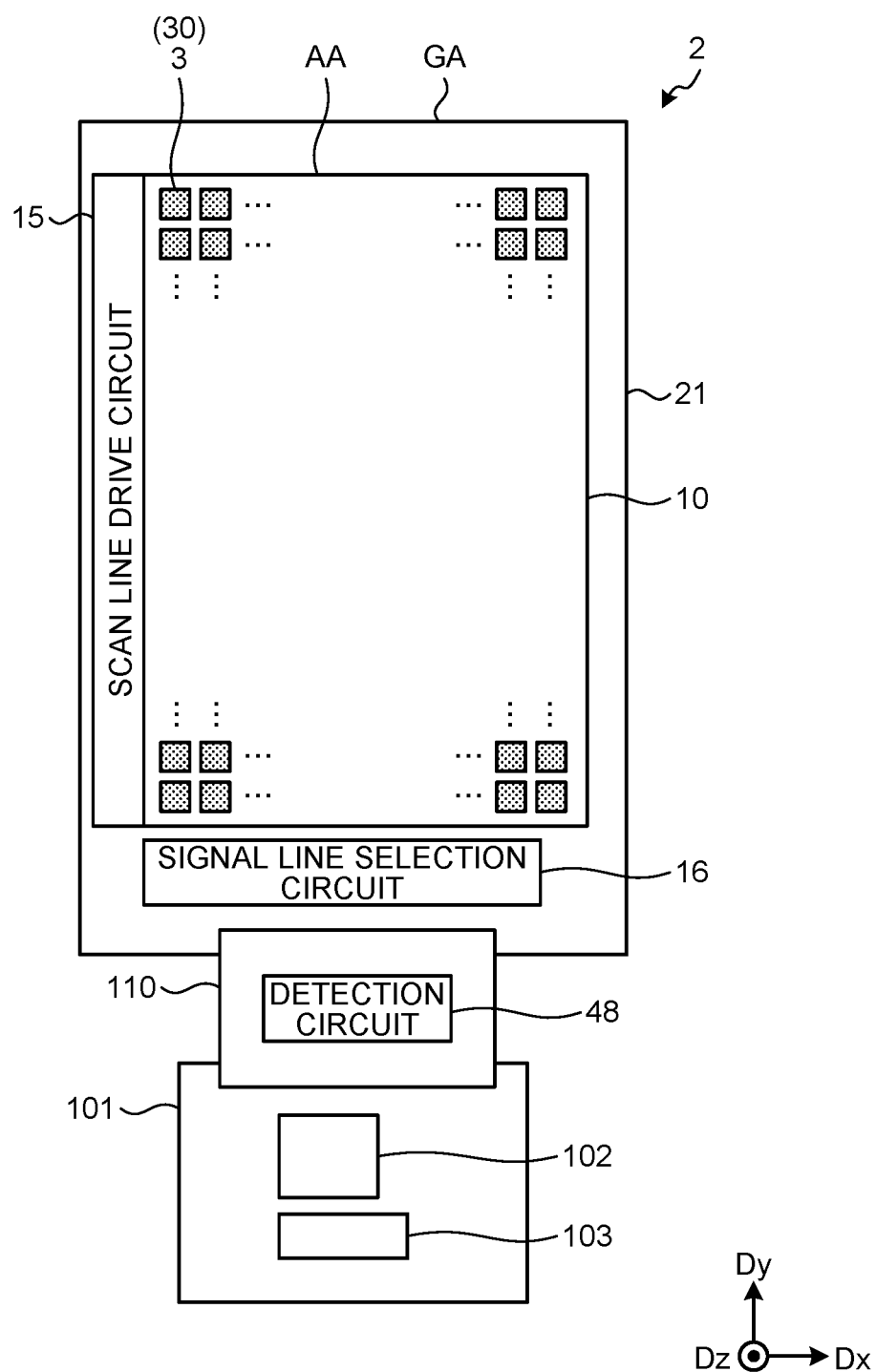
Figure 3:
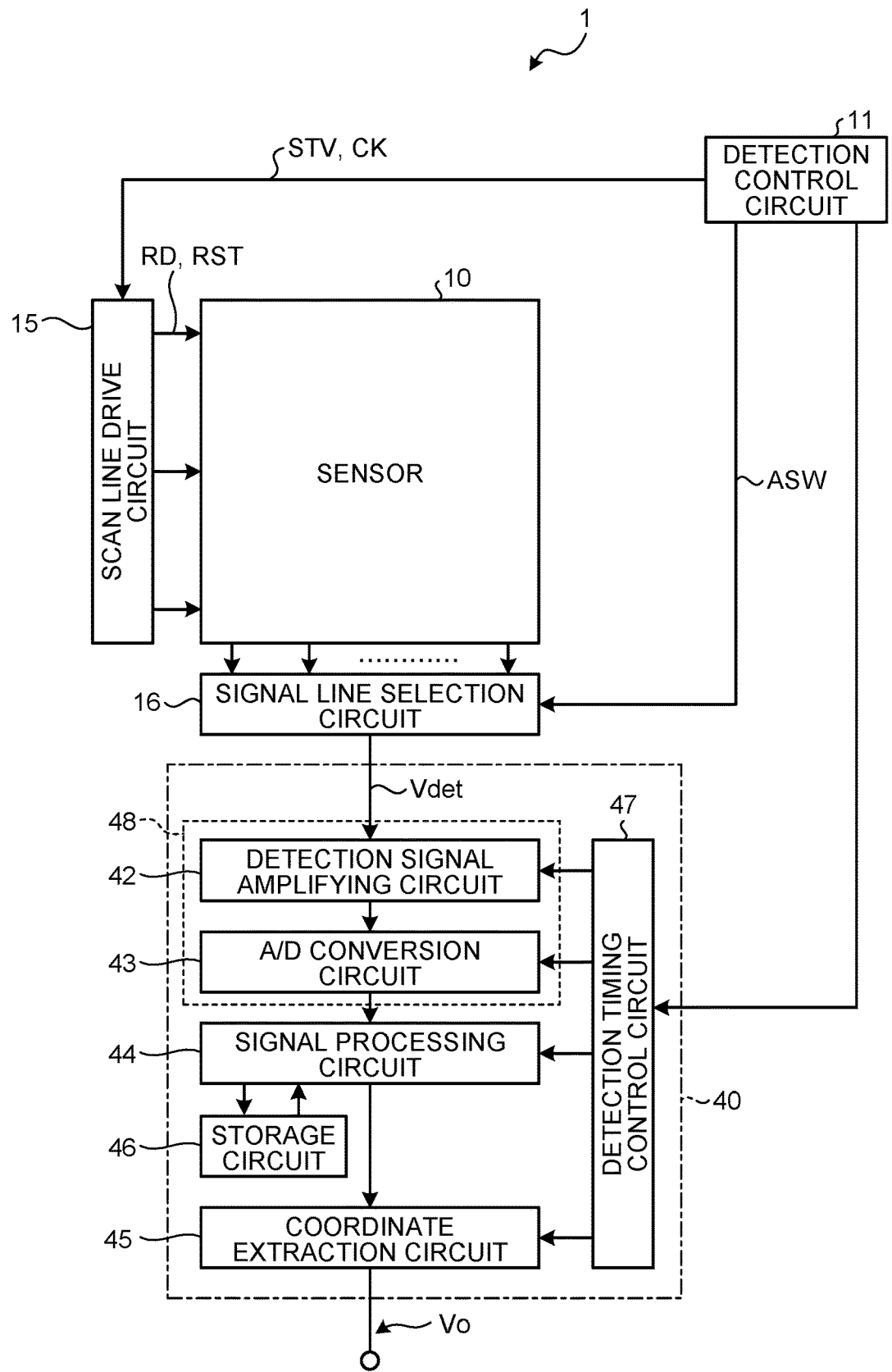

X: —O—, —S—, >CO, >C—R$_2$, >SO$_2$, —C(=O)—O—, —C(=O)—O-ϕ-O—C(=O)—
where R: —H, —CH$_3$, —CF$_3$,
Y: S, Se, Te,
m: 2, 4, 6, 8, 10, and
n: three or more oligomers or polymers FIG. 2 is a plan view illustrating a sensor substrate according to the first embodiment;

FIG. 3 is a block diagram illustrating a configuration example of a detection device according to the first embodiment;

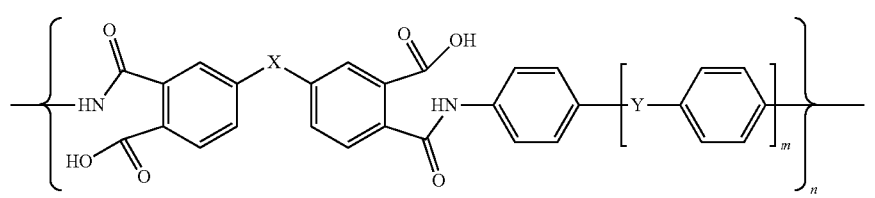

(4)

X: —O—, —S—, >CO, >C—R$_2$, >SO$_2$, —C(=O)—O—, —C(=O)—O-ϕ-O—C(=O)—
where R: —H, —CH$_3$, —CF$_3$,
Y: S, Se, Te,
m: 2, 4, 6, 8, 10, and
n: three or more oligomers or polymers An optical sensor according to an aspect of the present disclosure includes: a substrate; and a sensor stacked on the substrate. The sensor includes a photoelectric conversion element including a detection electrode, an electron transport layer, an active layer, a hole transport layer, and a counter electrode and stacked on the substrate. The active layer is formed of a polyimide-based material having a repeating unit represented by Chemical Formula 5 below.

Figure 4:
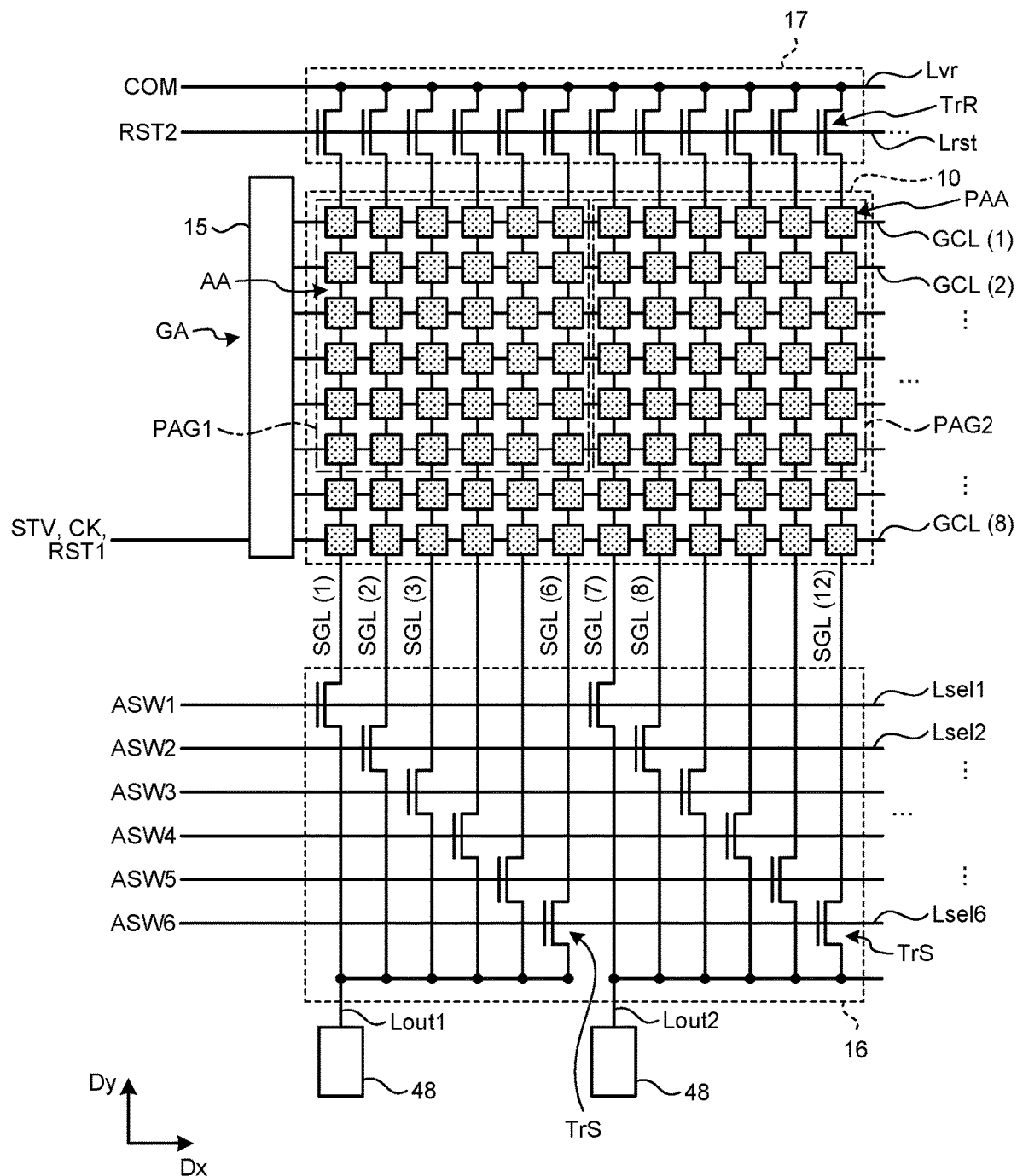
Figure 5:
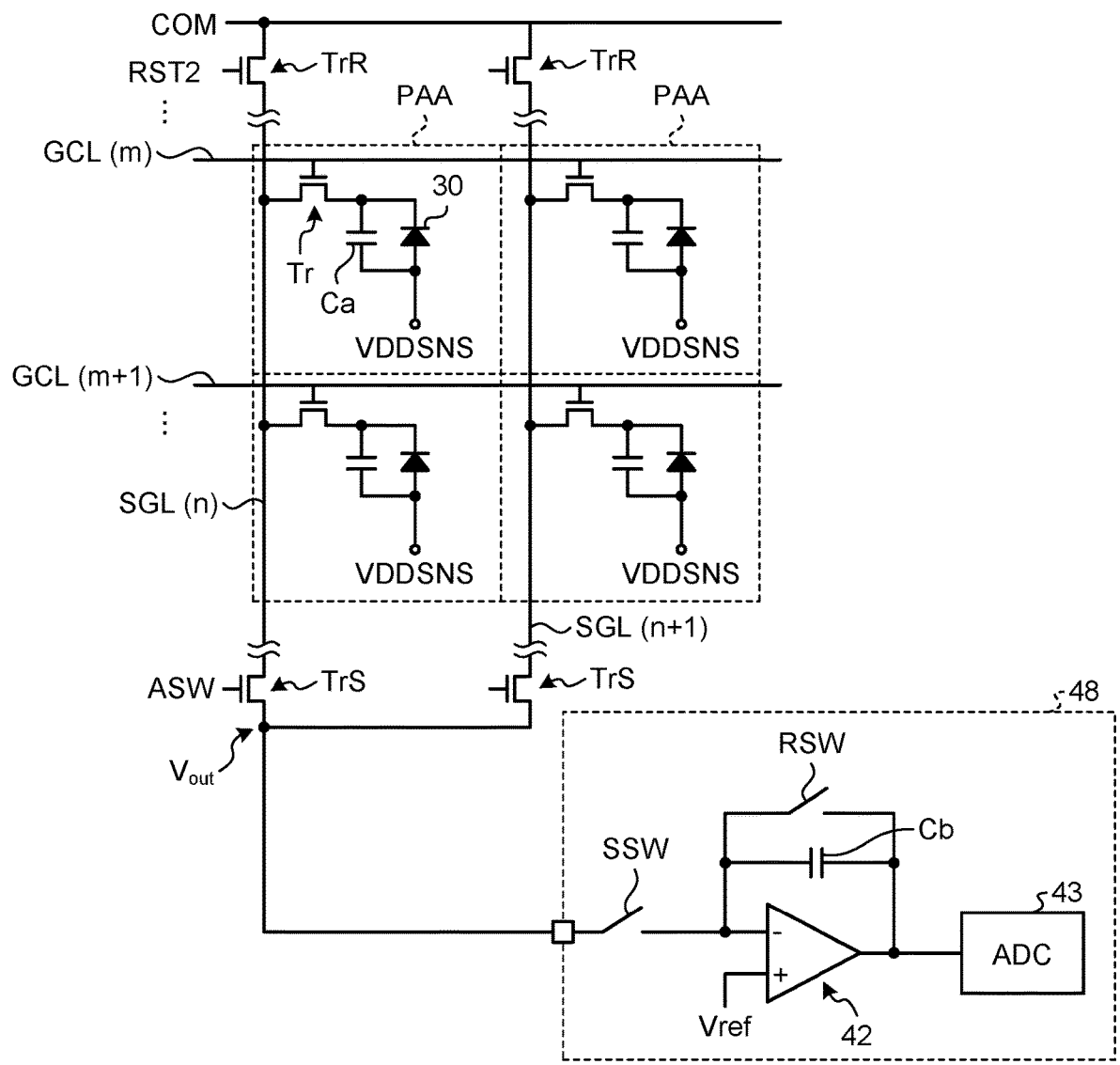
Figure 6:
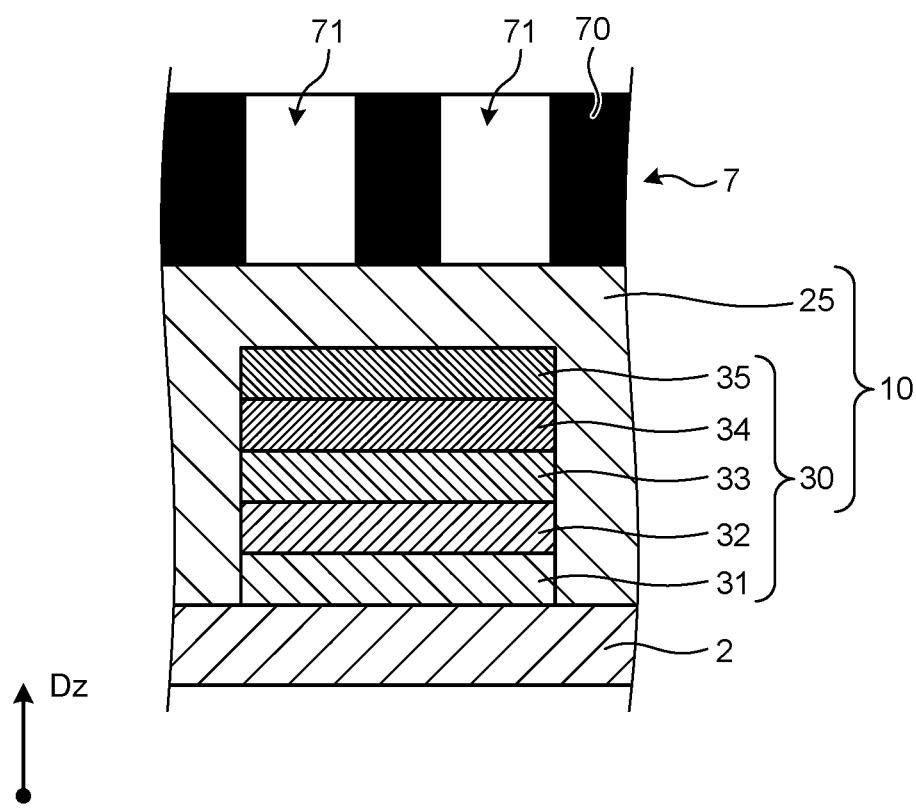
Figure 7:
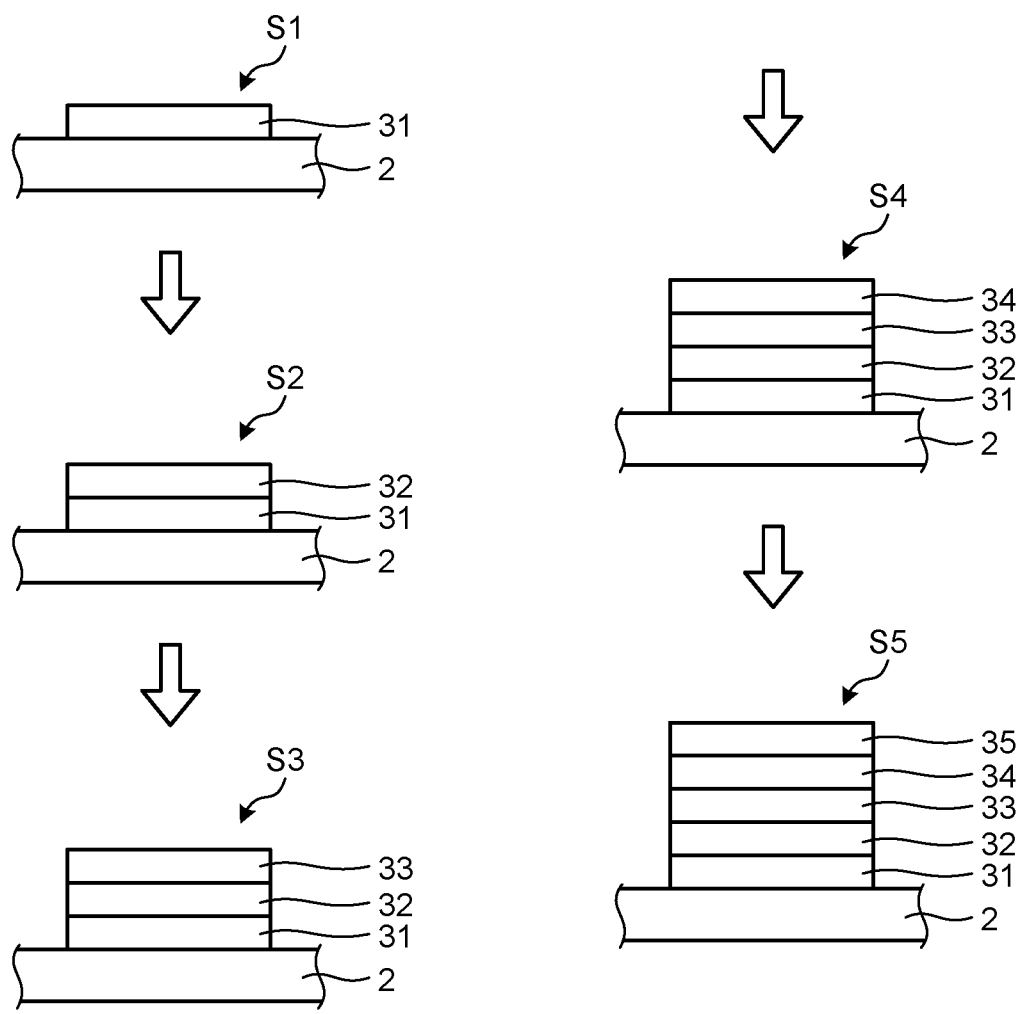
Figure 8:
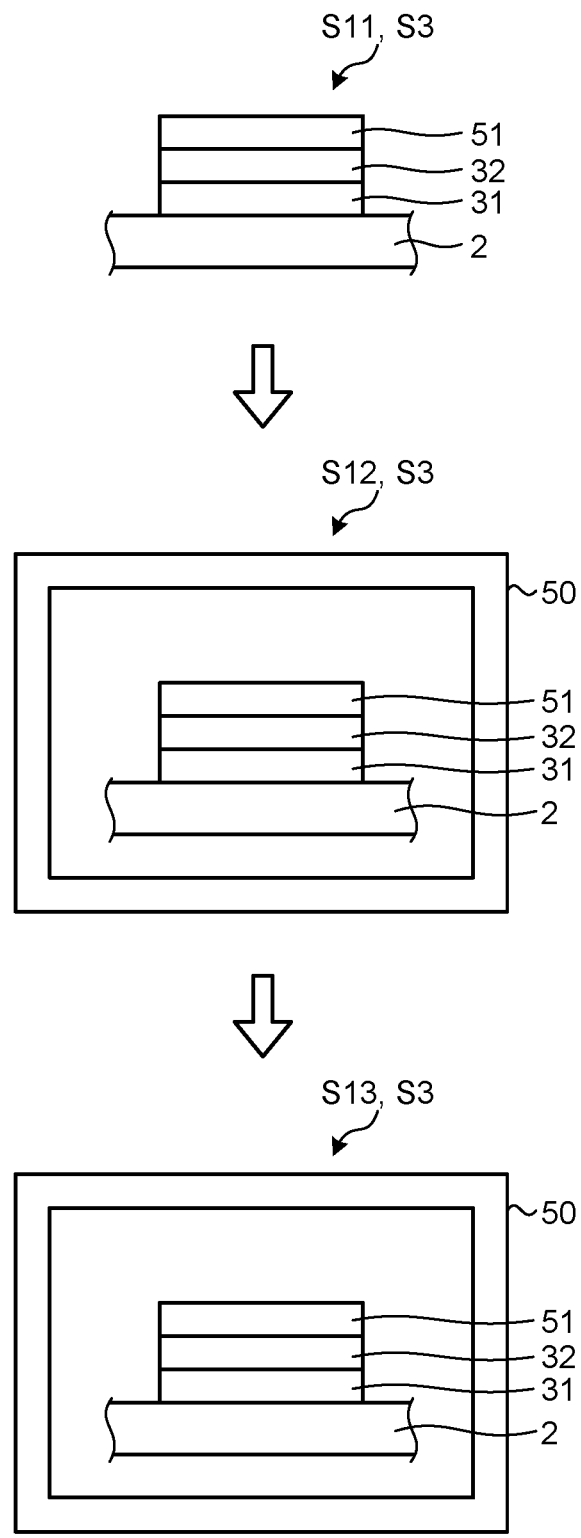
Figure 9:
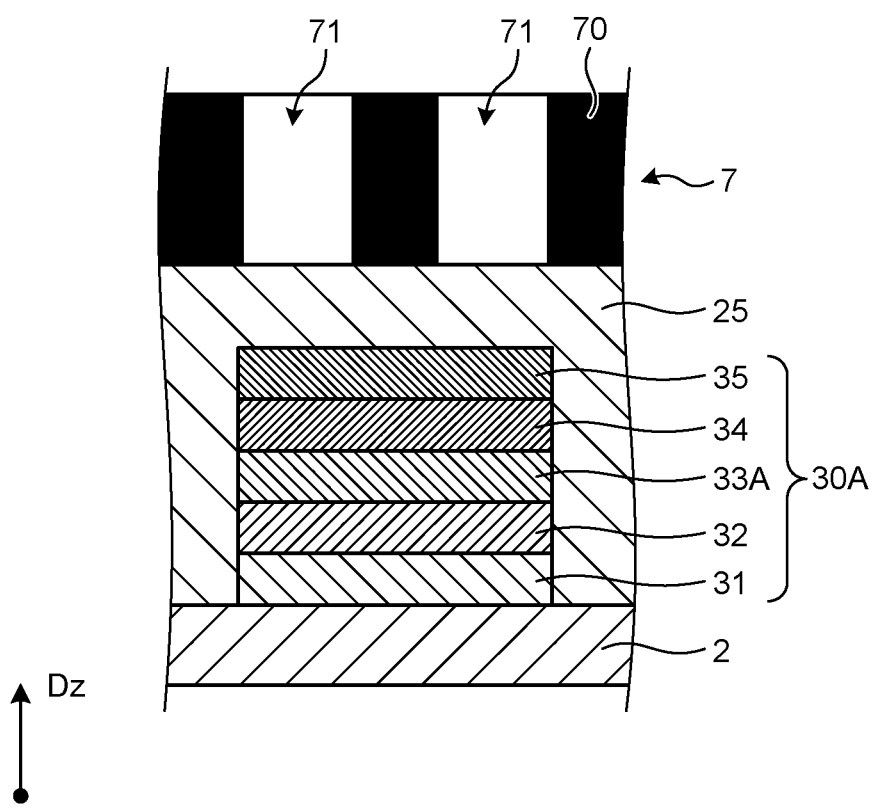

FIG. 4 is a circuit diagram illustrating the detection device according to the first embodiment;

FIG. 5 is a circuit diagram illustrating a plurality of partial detection areas of the first embodiment;

FIG. 6 is a sectional view illustrating a schematic sectional configuration of a sensor;

FIG. 7 is a diagram illustrating a manufacturing process of a photodiode according to the first embodiment;

FIG. 8 is a diagram illustrating a manufacturing process of an active layer according to the first embodiment;

FIG. 9 is a sectional view illustrating a schematic sectional configuration of a sensor according to a second embodiment of the present disclosure;

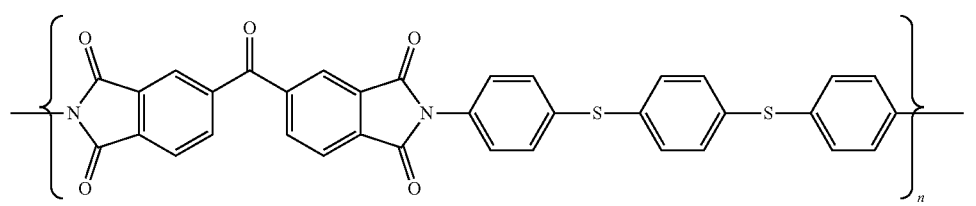

(5)

Figure 10:
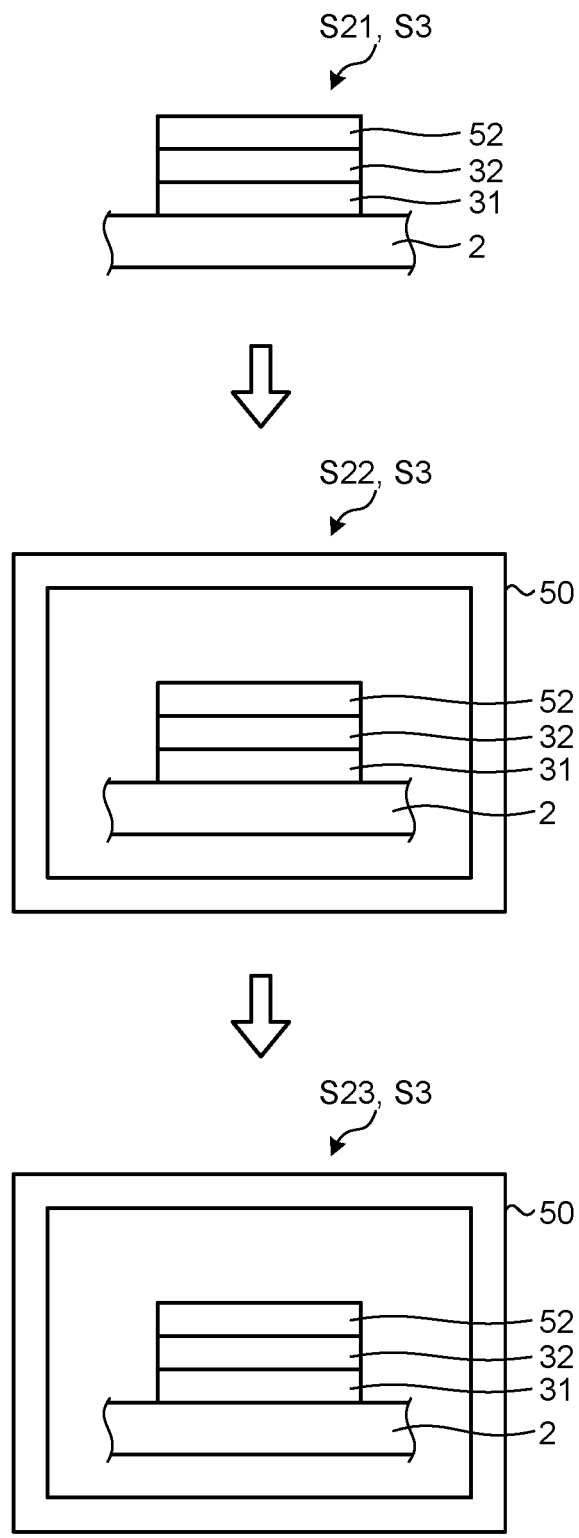
Figure 11:
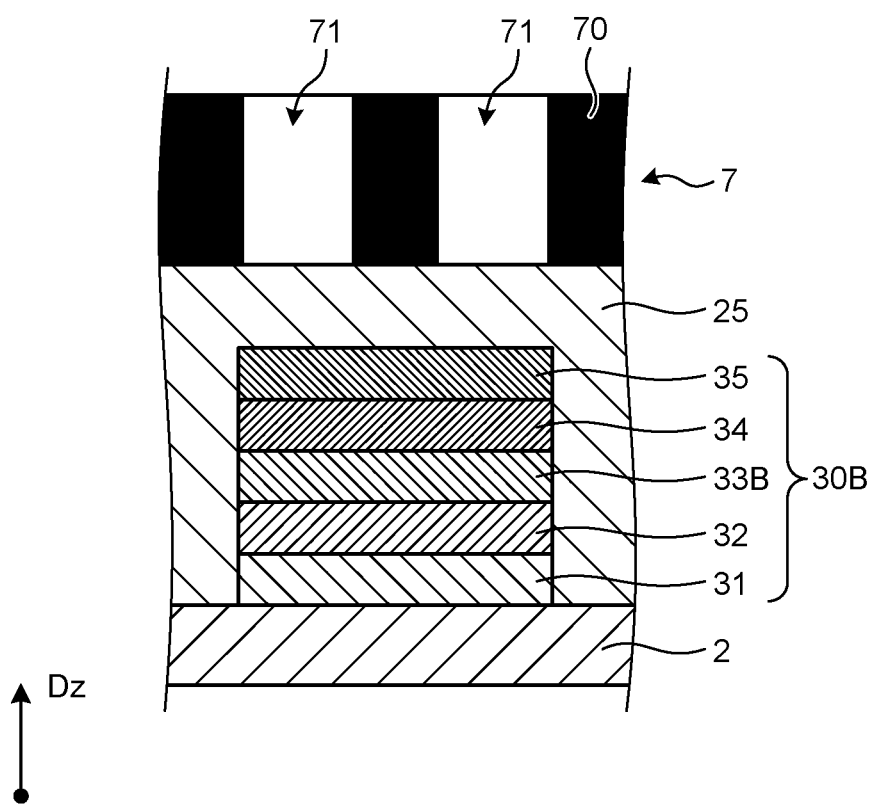
Figure 12:
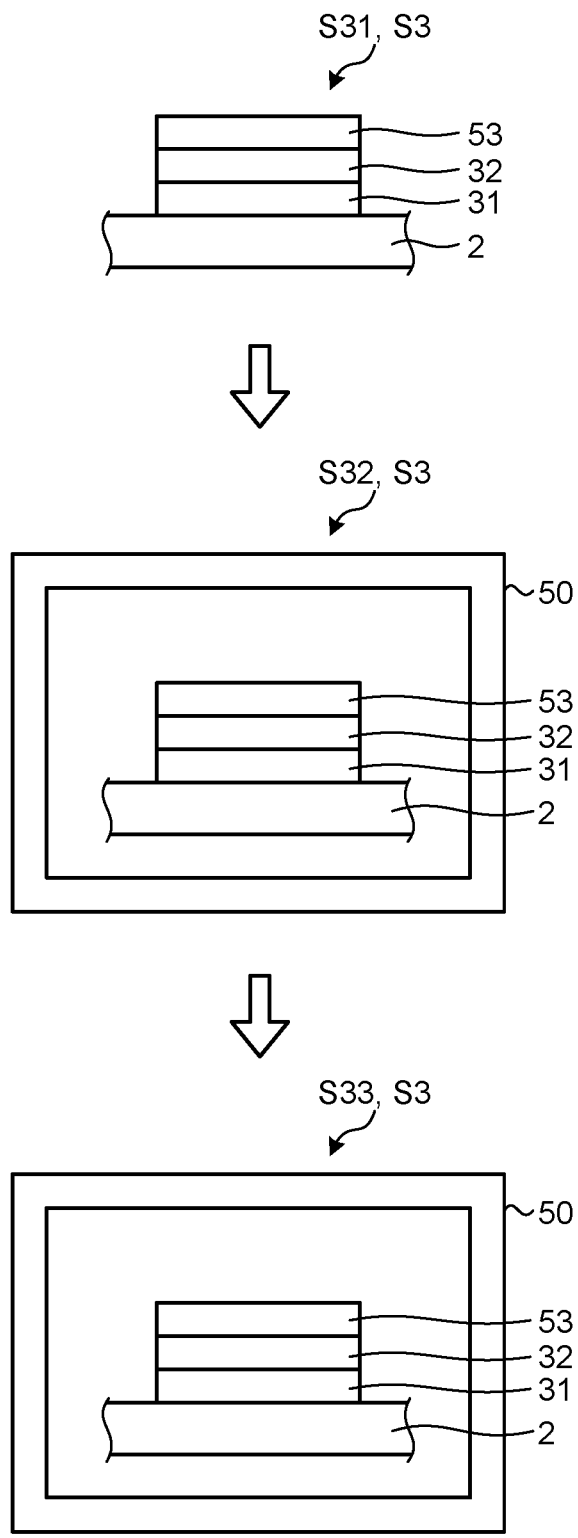
Figure 13:
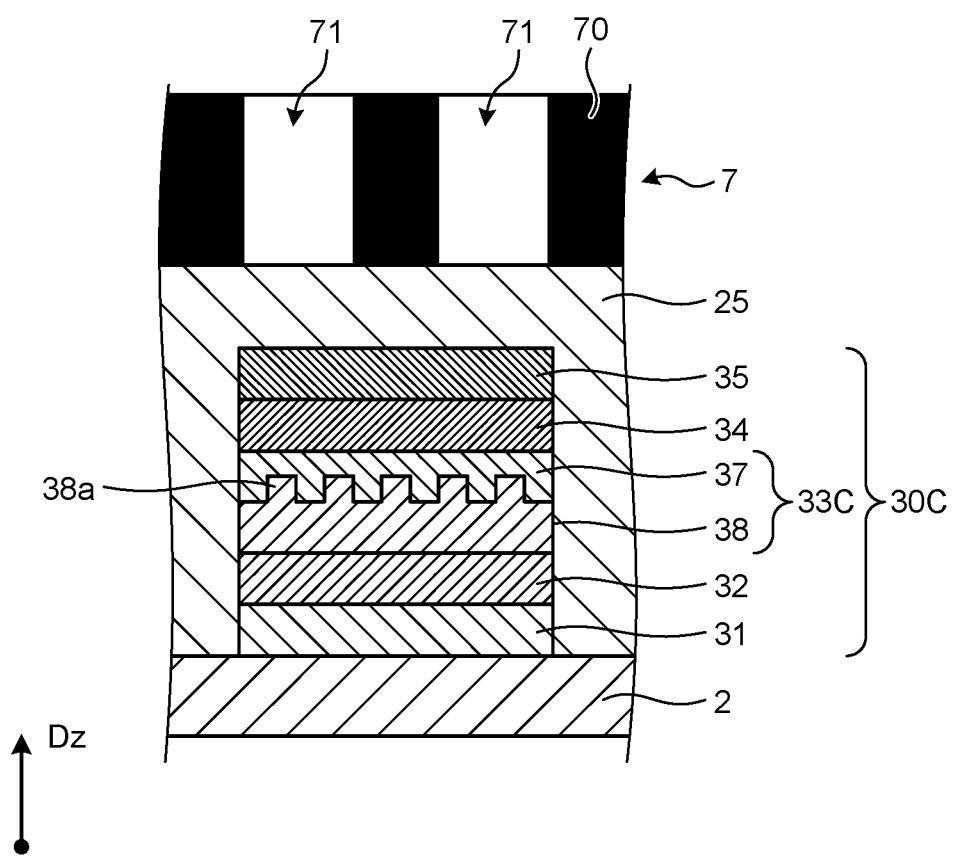
Figure 14:
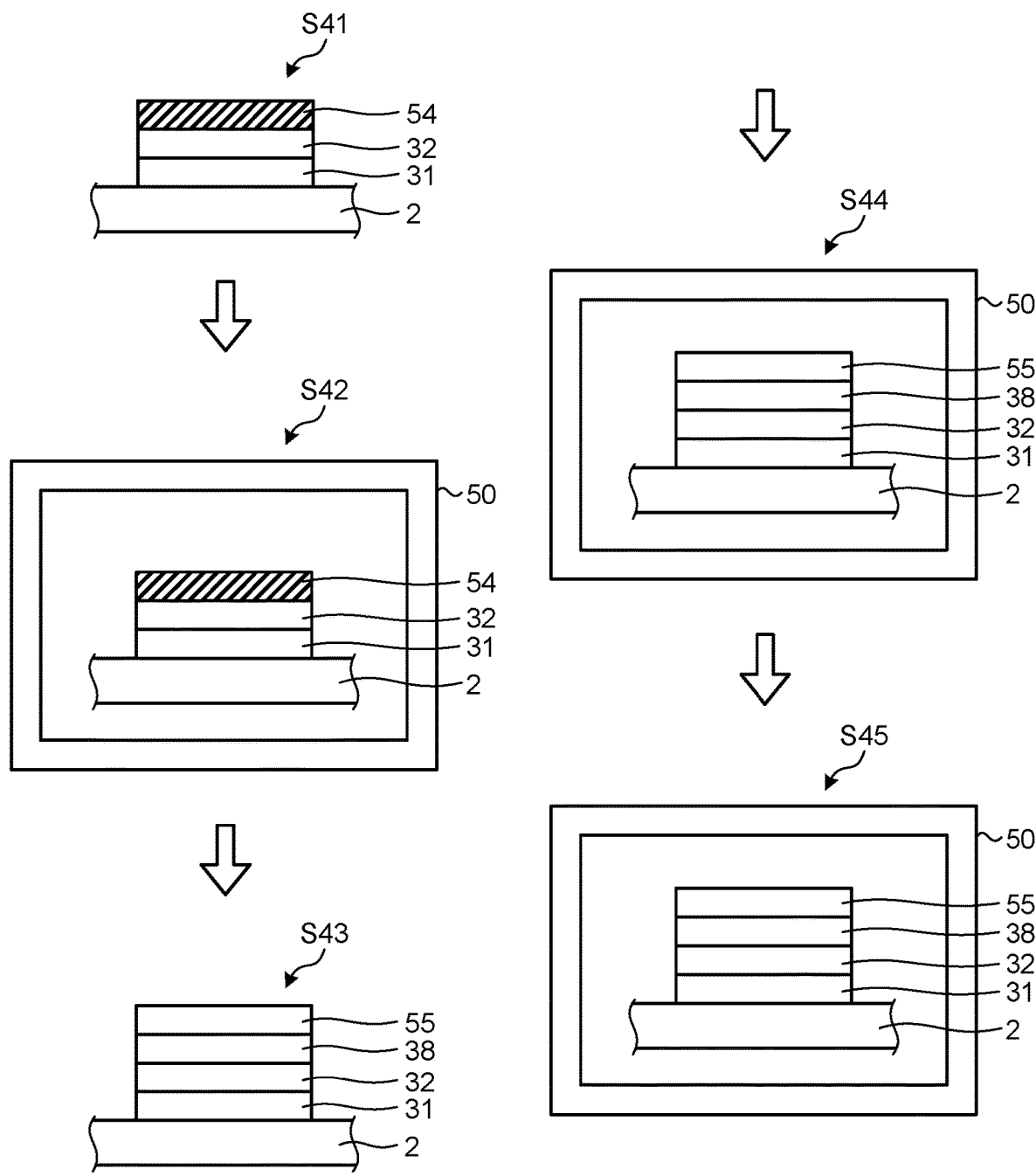
Figure 15:
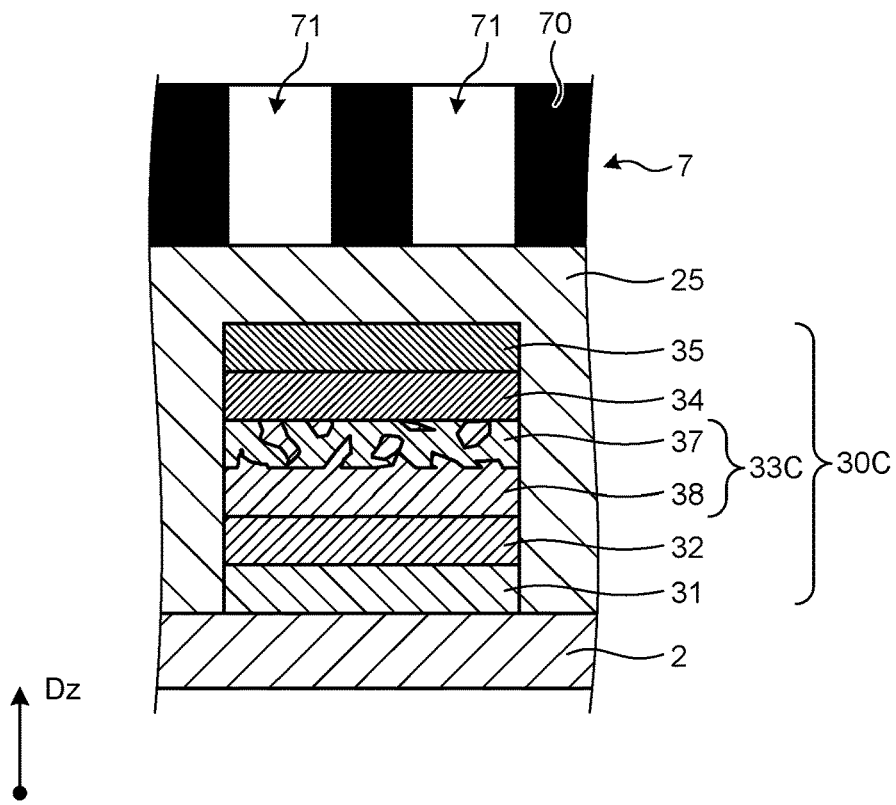
Figure 16:
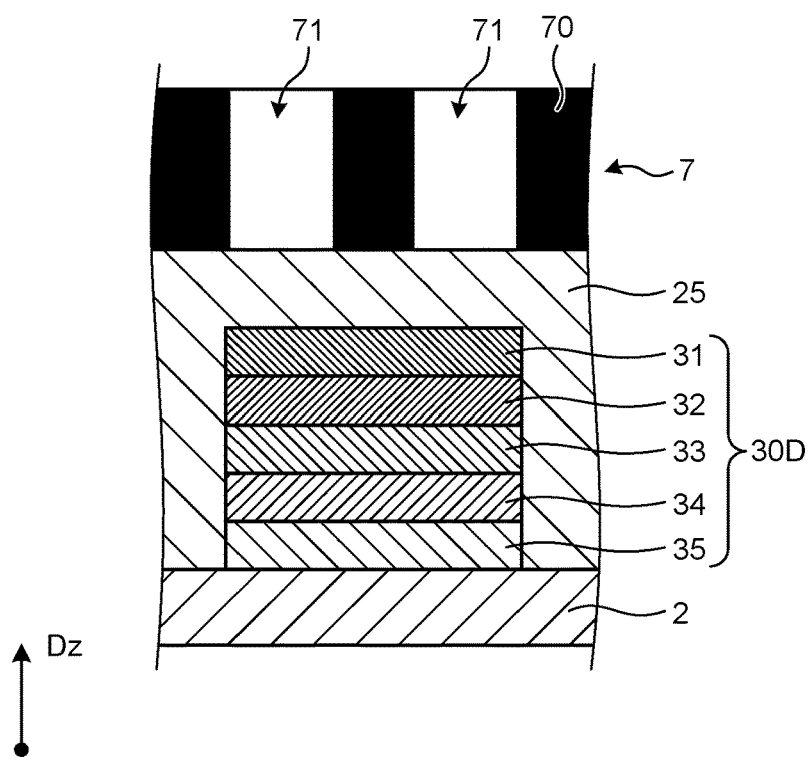
Figure 17:
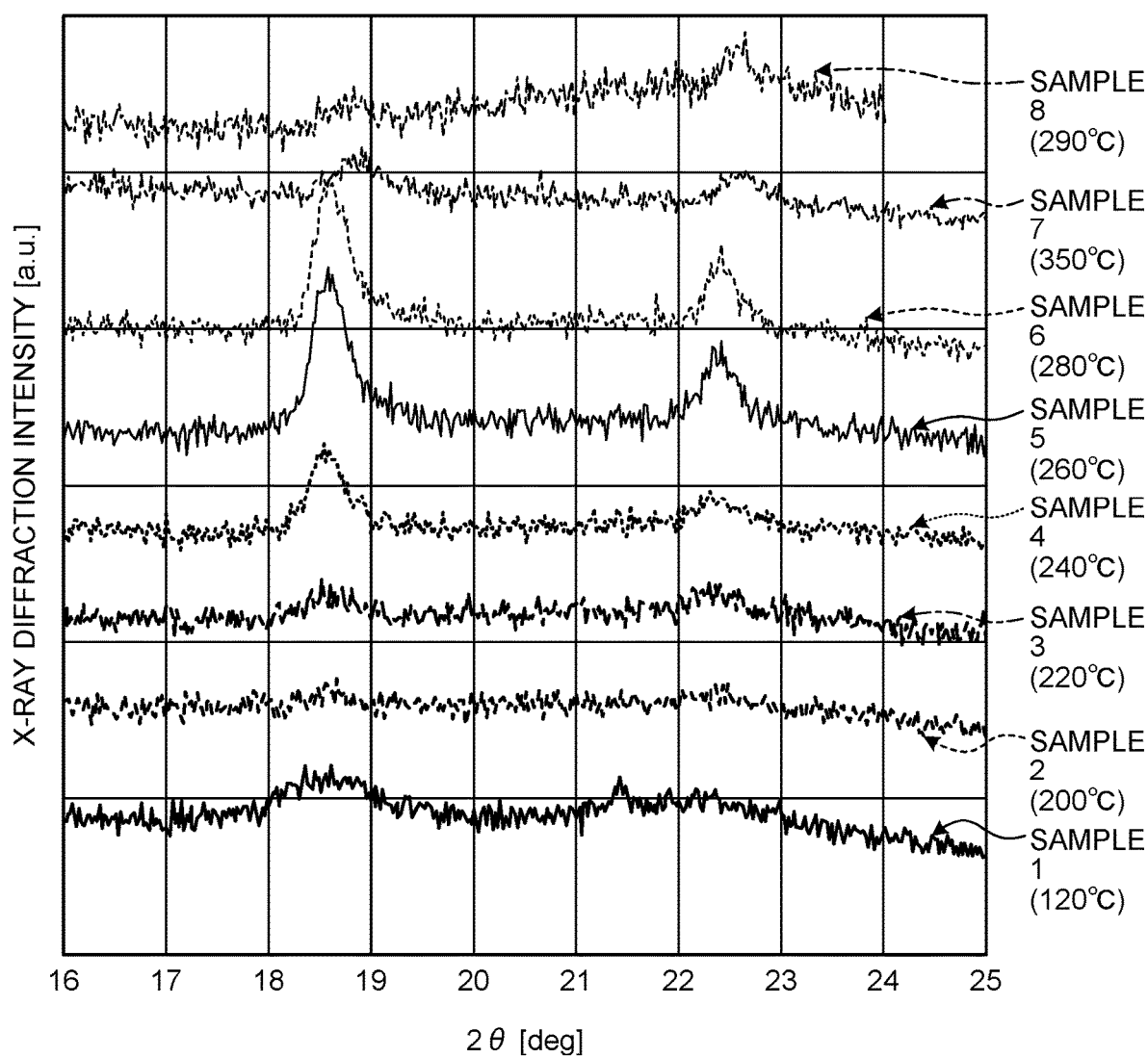
Figure 18:
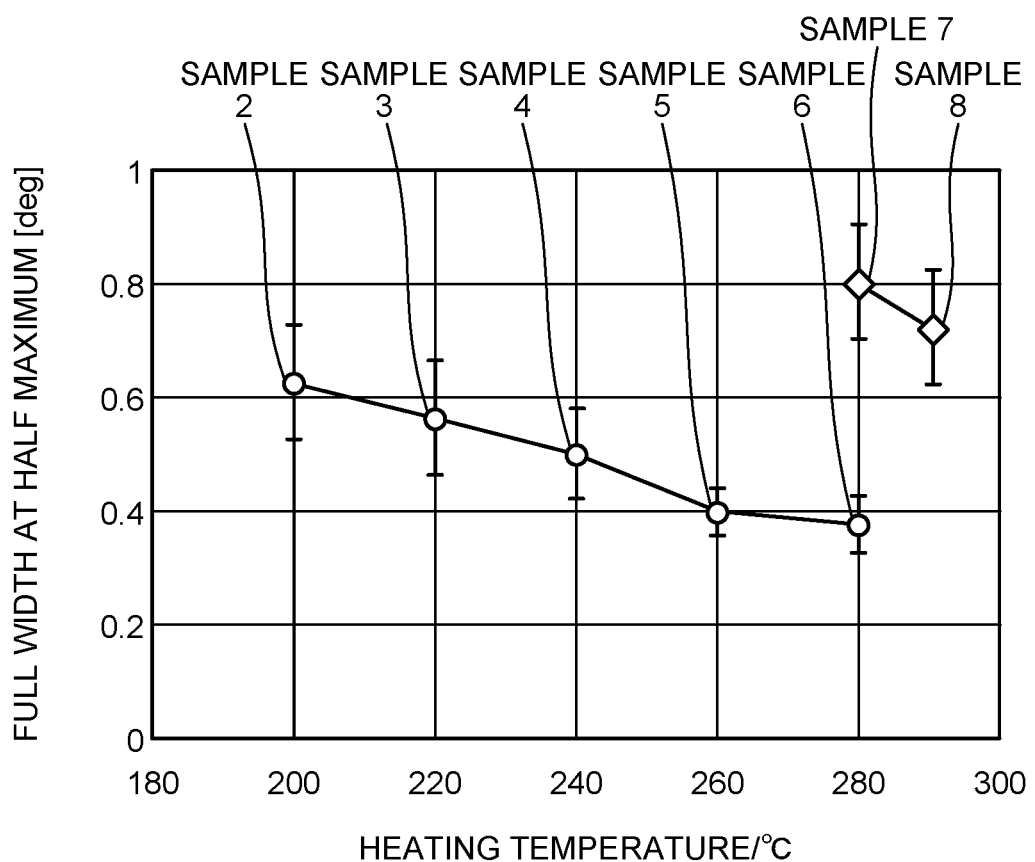
Figure 19:
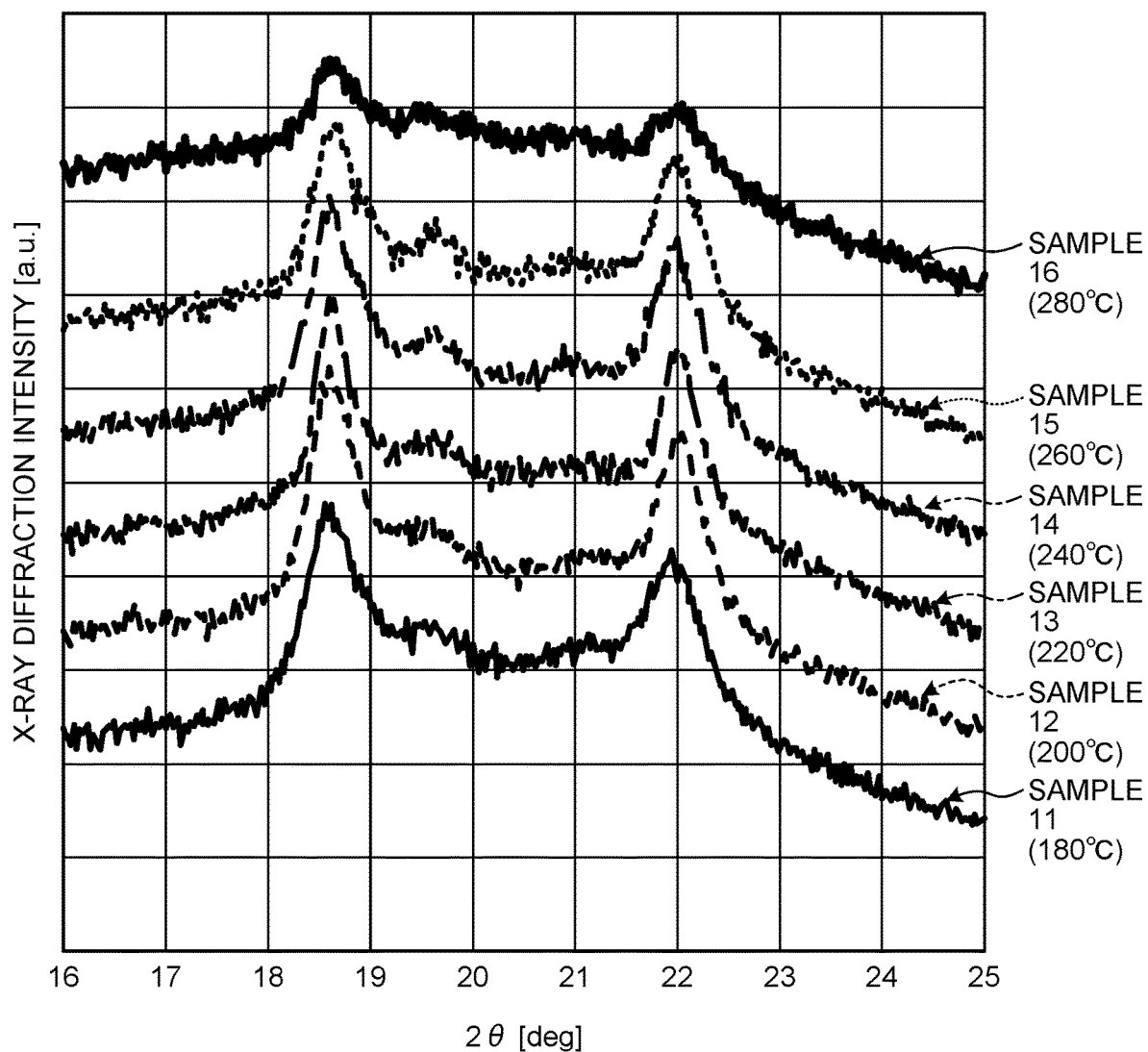
Figure 20:
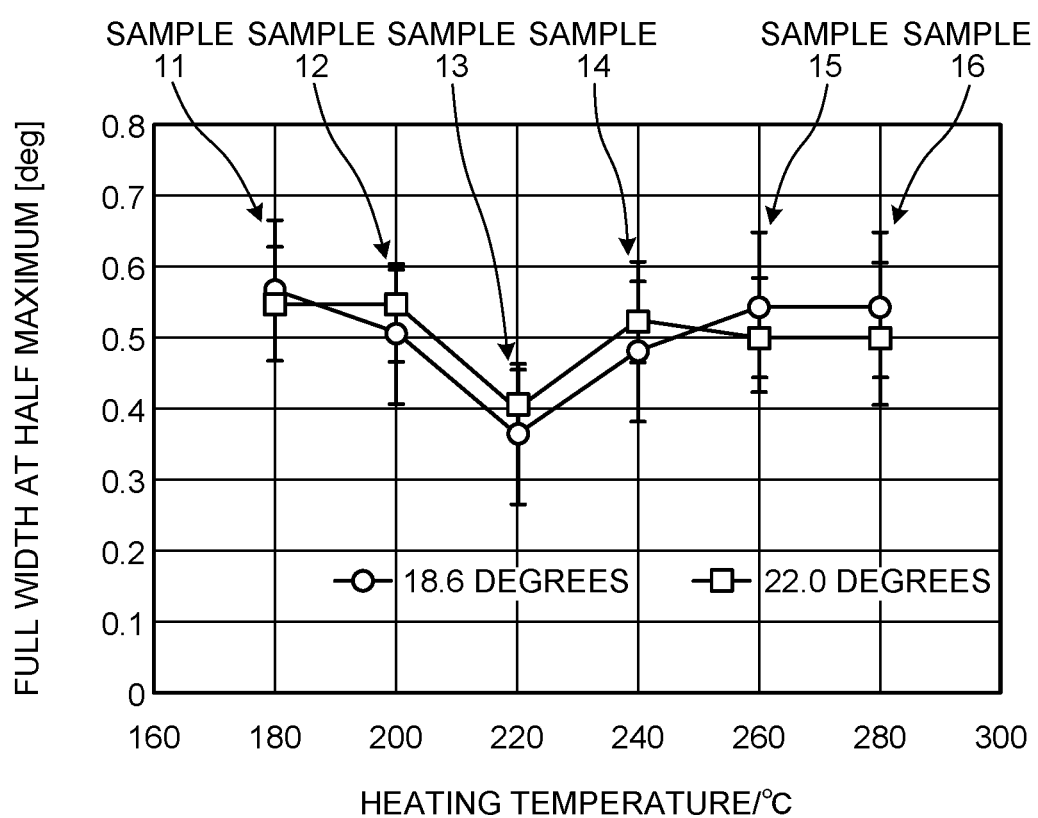

FIG. 10 is a diagram illustrating a manufacturing process of an active layer according to the second embodiment;

FIG. 11 is a sectional view illustrating a schematic sectional configuration of a sensor according to a third embodiment of the present disclosure;

FIG. 12 is a diagram illustrating a manufacturing process of an active layer according to the third embodiment;

FIG. 13 is a sectional view illustrating a schematic sectional configuration of a sensor according to a fourth embodiment of the present disclosure;

FIG. 14 is a diagram illustrating a manufacturing process of an active layer according to the fourth embodiment;

FIG. 15 is a sectional view illustrating a modification of the active layer of the fourth embodiment;

FIG. 16 is a sectional view illustrating a modification of a photoelectric conversion element;

FIG. 17 is a chart illustrating X-ray diffraction analysis results of Samples 1 to 8;

FIG. 18 is a graph illustrating a relation between a full width at half maximum of an X-ray spectrum and the substrate temperature at the time of film formation in Samples 2, 3, 4, 5, 6, 7, and 8;

FIG. 19 is a chart illustrating X-ray diffraction analysis results of Samples 11 to 16; and FIG. 20 is a graph illustrating a relation between the full width at half maximum of the X-ray spectrum and the substrate temperature at the time of film formation in Samples 11 to 16.

DETAILED DESCRIPTION

The following describes modes (embodiments) for carrying out the present disclosure in detail with reference to the drawings. The present disclosure is not limited to the description of the embodiments given below. Components described below include those easily conceivable by those skilled in the art or those substantially identical thereto. In addition, the components described below can be combined as appropriate. What is disclosed herein is merely an example, and the present disclosure naturally encompasses appropriate modifications easily conceivable by those skilled in the art while maintaining the gist of the present disclosure. To further clarify the description, widths, thicknesses, shapes, and the like of various parts may be schematically illustrated in the drawings as compared with actual aspects thereof. However, they are merely examples, and interpretation of the present disclosure is not limited thereto. The same component as that described with reference to an already mentioned drawing is denoted by the same reference numeral through the description and the drawings, and detailed description thereof may not be repeated where appropriate.

In the present specification and claims, in expressing an aspect of disposing another structure on or above a certain structure, a case of simply expressing "on" includes both a case of disposing the other structure immediately on the certain structure so as to contact the certain structure and a case of disposing the other structure above the certain structure with still another structure interposed therebetween, unless otherwise specified.

First Embodiment

Figure 1A:
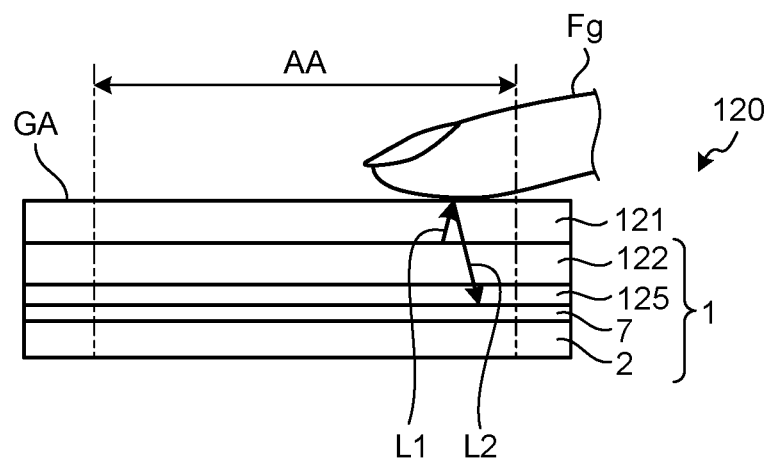
FIG. 1A is a sectional view of an optical sensor according to a first embodiment of the present disclosure.
Figure 1B:
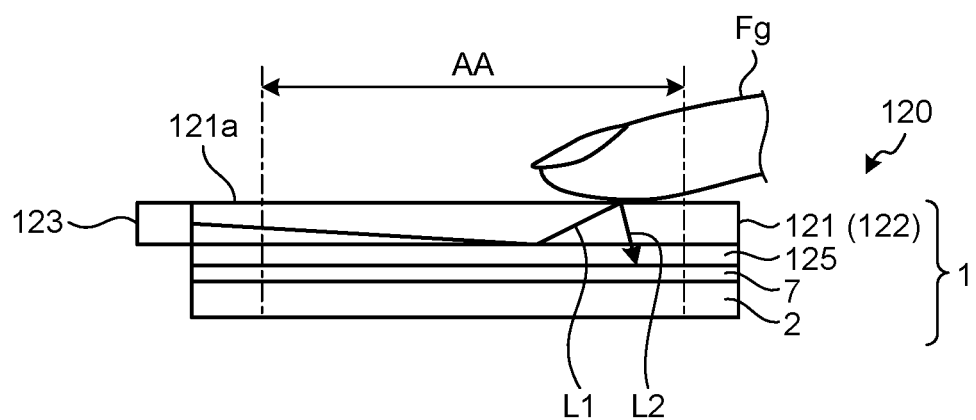
FIG. 1B is a sectional view of the optical sensor according to a first modification.
Figure 1C:
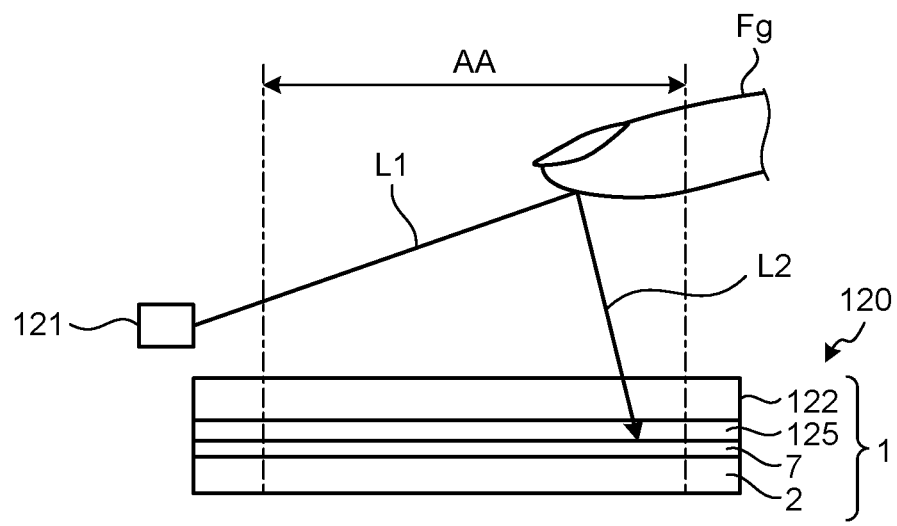
FIG. 1C is sectional view of the optical sensor according to a second modification.
Figure 1D:
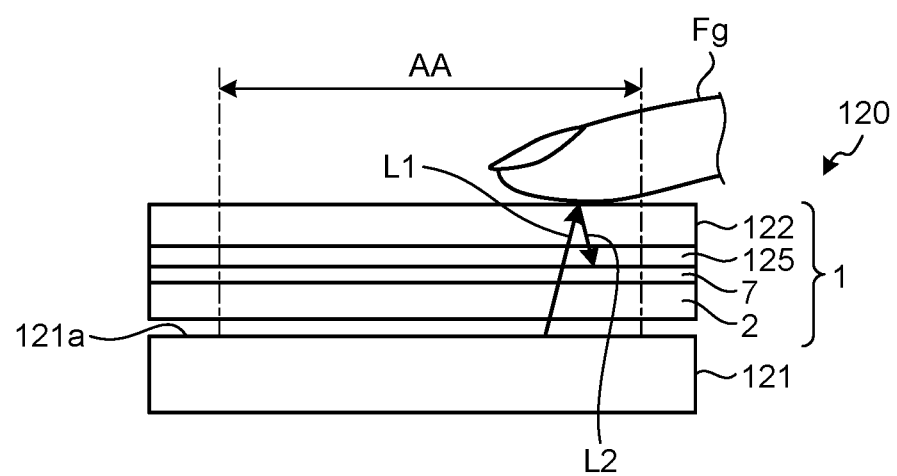
FIG. 1D is a sectional view of the optical sensor according to a third modification.

FIG. 1A is a sectional view of an optical sensor according to a first embodiment of the present disclosure. FIG. 1B is a sectional view of the optical sensor according to a first modification. FIG. 1C is sectional view of the optical sensor according to a second modification. FIG. 1D is a sectional view of the optical sensor according to a third modification.

In the description of the embodiment, a case where a photoelectric conversion element (referred to as a photodiode 30 in the embodiment) is applied to an optical sensor 120 will be used as an example. As illustrated in FIG. 1A, the optical sensor 120 is a detection apparatus having an illumination device, the detection apparatus including a detection device 1 and an illumination device 121. The detection device 1 includes a sensor substrate 2, an optical filter 7, an adhesive layer 125, and a cover member 122. The sensor substrate 2, the optical filter 7, the adhesive layer 125, the cover member 122, and the illumination device 121 are stacked in this order in a direction orthogonal to a surface of the sensor substrate 2.

The adhesive layer 125 bonds the optical filter 7 to the cover member 122. The adhesive layer 125 need not bond together the entire surfaces of the optical filter 7 and the cover member 122. For example, the structure may be such that an area corresponding to a detection area AA is not bonded and only an area corresponding to a peripheral area GA is bonded. The cover member 122 is a member for protecting the sensor substrate 2 and the optical filter 7 and covers the sensor substrate 2 and the optical filter 7. The cover member 122 is, for example, a glass substrate.

The illumination device 121 can be a light source or a display panel of, for example, light-emitting diodes (LEDs). The display panel may be, for example, an organic electroluminescent (EL) diode (organic light-emitting diode (OLED)) panel or an inorganic EL display (micro-LED or mini-LED) panel. Alternatively, the display panel may be a liquid crystal display (LCD) panel using liquid crystal elements as display elements or an electrophoretic display (EPD) panel using electrophoretic elements as display elements.

In such an optical sensor 120, light L1 emitted from the illumination device 121 is reflected by a finger Fg. The detection device 1 detects light L2 reflected by the finger Fg and detects asperities (such as a fingerprint) on a surface of the finger Fg. The detection device 1 may detect information on a living body by detecting the light L2 reflected inside the finger Fg in addition to detecting the fingerprint. Examples of the information on the living body include a blood vessel image of, for example, a vein; pulsation; and a pulse wave. The color of the light L1 emitted from the illumination device 121 may be varied depending on a detection target.

The optical sensor 120 is not limited to the example illustrated in FIG. 1A. As illustrated in FIG. 1B, the illumination device 121 may be, for example, what is called a side light-type front light that uses a cover member 122 as a light guide plate provided in a position corresponding to the detection area AA of the detection device 1 and includes a plurality of light sources 123 arranged side by side at one end or both ends of the cover member 122. In other words, the cover member 122 has a light-emitting surface 121a that emits light and serves as a component of the illumination device 121. According to this illumination device 121, the light L1 is emitted from the light-emitting surface 121a of the cover member 122 toward the finger Fg, serving as the detection target. For example, LEDs for emitting light in a predetermined color are used as the light sources.

As illustrated in FIG. 1C, the illumination device 121 may be provided on a lateral side or above the cover member 122 to emit the light L1 to the finger Fg from the lateral side or above the finger Fg.

As illustrated in FIG. 1D, the illumination device 121 may be what is called a direct-type backlight that is provided on the back side of the detection device 1.

In addition, although not illustrated, the illumination device 121 itself may serve as the cover member 122. Alternatively, sunlight reflected by the finger Fg may be detected without providing the illumination device 121.

FIG. 2 is a plan view illustrating the sensor substrate according to the first embodiment. A first direction Dx illustrated in FIG. 2 and later drawings is one direction in a plane parallel to a substrate 21. A second direction Dy is one direction in the plane parallel to the substrate 21, and is a direction orthogonal to the first direction Dx. The second direction Dy may intersect the first direction Dx without being orthogonal thereto. A third direction Dz is a direction orthogonal to the first direction Dx and the second direction Dy, and is a direction normal to the substrate 21.

As illustrated in FIG. 2, the sensor substrate 2 includes the substrate 21, a sensor 10, a scan line drive circuit 15, a signal line selection circuit 16, a detection circuit 48, a control circuit 102, and a power supply circuit 103.

The substrate 21 is a drive circuit board that includes a thin-film transistor (TFT) such as a switching element Tr and various types of wiring such as gate lines GCL and signal lines SGL and drives the sensor 10. The substrate 21 is also called a backplane or an array substrate. The substrate 21 is electrically coupled to a control substrate 101 through a wiring substrate 110. The wiring substrate 110 is, for example, a flexible printed circuit board or a rigid circuit board. The wiring substrate 110 is provided with the detection circuit 48. The control substrate 101 is provided with the control circuit 102 and the power supply circuit 103. The control circuit 102 is, for example, a field-programmable gate array (FPGA). The control circuit 102 supplies control signals to the sensor 10, the scan line drive circuit 15, and the signal line selection circuit 16. The power supply circuit 103 supplies voltage signals including, for example, a sensor power supply signal VDDSNS (refer to FIG. 5) to the sensor 10, the scan line drive circuit 15, and the signal line selection circuit 16. Although the present embodiment exemplifies the case of disposing the detection circuit 48 on the wiring substrate 110, the present disclosure is not limited to this case, and the detection circuit 48 may be disposed on the substrate 21.

The substrate 21 has the detection area AA and the peripheral area GA. Each element (detection element 3) of the sensor 10 is provided in the detection area AA. The peripheral area GA is an area outside the detection area AA and is an area not provided with the element (detection element 3). The scan line drive circuit 15 and the signal line selection circuit 16 are provided in the peripheral area GA.

The sensor 10 is provided with a plurality of the detection elements 3 as optical sensors. The detection element 3 is the photodiode 30. The photodiode 30 is a photoelectric conversion element and outputs an electrical signal corresponding to light irradiating each of the photodiodes 30. More specifically, the photodiode 30 is an organic photodiode (OPD). The detection elements 3 (photodiodes 30) are arranged in a matrix having a row-column configuration in the detection area AA. The photodiode 30 performs the detection according to a gate drive signal (for example, a reset control signal RST or a read control signal RD) supplied from the scan line drive circuit 15. Each of the photodiodes 30 outputs the electrical signal corresponding to the light irradiating the photodiode 30 as a detection signal Vdet to the signal line selection circuit 16. The detection device 1 detects the information on the living body based on the detection signals Vdet received from the photodiodes 30.

FIG. 3 is a block diagram illustrating a configuration example of the detection device according to the first embodiment. As illustrated in FIG. 3, the detection device 1 further includes a detection control circuit 11 and a detector 40. One, some, or all functions of the detection control circuit 11 are included in the control circuit 102. One, some, or all functions of the detector 40 other than those of the detection circuit 48 are also included in the control circuit 102.

The detection control circuit 11 is a circuit that supplies control signals to the scan line drive circuit 15, the signal line selection circuit 16, and the detector 40 to control operations of these components. The detection control circuit 11 supplies various control signals including, for example, a start signal STV and a clock signal CK to the scan line drive circuit 15. The detection control circuit 11 also supplies various control signals including, for example, a selection signal ASW to the signal line selection circuit 16.

The scan line drive circuit 15 is a circuit that drives a plurality of scan lines (gate lines GCL (refer to FIG. 4)) based on the various control signals. The scan line drive circuit 15 sequentially or simultaneously selects the scan lines and supplies the gate drive signal to the selected scan lines. Through this operation, the scan line drive circuit 15 selects the photodiodes 30 coupled to the scan lines.

The signal line selection circuit 16 is a switch circuit that sequentially or simultaneously selects the signal lines SGL (refer to FIG. 4). The signal line selection circuit 16 is, for example, a multiplexer. The signal line selection circuit 16 couples the selected output signal lines SL to the detection circuit 48 based on the selection signal ASW supplied from the detection control circuit 11. Through this operation, the signal line selection circuit 16 outputs the detection signals Vdet of the photodiodes 30 to the detector 40.

The detector 40 includes the detection circuit 48, a signal processing circuit 44, a coordinate extraction circuit 45, a storage circuit 46, and a detection timing control circuit 47. The detection timing control circuit 47 performs control to cause the detection circuit 48, the signal processing circuit 44, and the coordinate extraction circuit 45 to operate in synchronization with one another based on a control signal supplied from the detection control circuit 11.

The detection circuit 48 is, for example, an analog front-end (AFE) circuit. The detection circuit 48 is a signal processing circuit having functions of at least a detection signal amplifying circuit 42 and an analog-to-digital (A/D) conversion circuit 43. The detection signal amplifying circuit 42 is a circuit that amplifies the detection signal Vdet, and is, for example, an integration circuit. The A/D conversion circuit 43 converts an analog signal output from the detection signal amplifying circuit 42 into a digital signal.

The signal processing circuit 44 is a logic circuit that detects a predetermined physical quantity received by the sensor 10 based on output signals of the detection circuit 48. The signal processing circuit 44 can detect asperities on a surface of the finger Fg or a palm based on the signals from the detection circuit 48 when the finger Fg is in contact with or in proximity to a detection surface. The signal processing circuit 44 may detect the information on the living body based on the signals from the detection circuit 48. Examples of the information on the living body include a blood vessel image, a pulse wave, pulsation, and blood oxygen saturation of the finger Fg or the palm.

The storage circuit 46 temporarily stores therein signals calculated by the signal processing circuit 44. The storage circuit 46 may be, for example, a random-access memory (RAM) or a register circuit.

The coordinate extraction circuit 45 is a logic circuit that obtains detected coordinates of the asperities on the surface of the finger Fg or the like when the contact or proximity of the finger Fg is detected by the signal processing circuit 44. The coordinate extraction circuit 45 is the logic circuit that also obtains detected coordinates of blood vessels of the finger Fg or the palm. The coordinate extraction circuit 45 combines the detection signals Vdet output from the respective detection elements 3 of the sensor 10 to generate two-dimensional information representing a shape of the asperities on the surface of the finger Fg or the like. The coordinate extraction circuit 45 may output the detection signals Vdet as sensor outputs Vo instead of calculating the detected coordinates.

The following describes a circuit configuration example of the detection device 1. FIG. 4 is a circuit diagram illustrating the detection device according to the first embodiment. As illustrated in FIG. 4, the sensor 10 has a plurality of partial detection areas PAA arranged in a matrix having a row-column configuration. Each of the partial detection areas PAA is provided with the photodiode 30.

The gate lines GCL extend in the first direction Dx and are coupled to the partial detection areas PAA arranged in the first direction Dx. A plurality of gate lines GCL(1), GCL(2), . . . , GCL(8) are arranged in the second direction Dy and are each coupled to the scan line drive circuit 15. In the following description, the gate lines GCL(1), GCL(2), . . . , GCL(8) will each be simply referred to as the gate line GCL when they need not be distinguished from one another. For ease of understanding of the description, FIG. 4 illustrates eight gate lines GCL. However, this is merely an example, and M gate lines GCL (where M is eight or larger, and is, for example, 256) may be arranged.

The signal lines SGL extend in the second direction Dy, and are coupled to the photodiodes 30 of the partial detection areas PAA arranged in the second direction Dy. A plurality of signal lines SGL(1), SGL(2), . . . , SGL(12) are arranged in the first direction Dx, and are each coupled to the signal line selection circuit 16 and a reset circuit 17. In the following description, the signal lines SGL(1), SGL(2), . . . , SGL(12) will each be simply referred to as the signal line SGL when they need not be distinguished from one another.

For ease of understanding of the description, 12 signal lines SGL are illustrated. However, this is merely an example, and N signal lines SGL (where N is 12 or larger, and is, for example, 252) may be arranged. In FIG. 4, the sensor 10 is provided between the signal line selection circuit 16 and the reset circuit 17. The configuration is not limited thereto. The signal line selection circuit 16 and the reset circuit 17 may be coupled to ends of the signal lines SGL on the same side. The substantial area of one sensor is, for example, 50×50 $\mu m^2$; the resolution of the detection area AA is, for example, 508 pixels per inch (ppi); the number of sensors arranged in the detection area AA is, for example, 252×256 cells; and the area of the detection area AA is, for example, 12.6×12.8 $mm^2$.

The scan line drive circuit 15 receives various control signals such as the start signal STV, the clock signal CK, and a reset signal RST1 from the control circuit 102 (refer to FIG. 2). The scan line drive circuit 15 sequentially selects the gate lines GCL(1), GCL(2), . . . , GCL(8) in a time-division manner based on the various control signals. The scan line drive circuit 15 supplies a gate drive signal Vgcl to the selected one of the gate lines GCL. This operation supplies the gate drive signal to a plurality of first switching elements Tr coupled to the gate line GCL, and corresponding ones of the partial detection areas PAA arranged in the first direction Dx are selected as the detection targets.

The scan line drive circuit 15 may perform different driving for each of detection modes including the detection of the fingerprint and the detection of different items of the information on the living body (such as the pulse wave, the pulsation, the blood vessel image, and the blood oxygen saturation level). For example, the scan line drive circuit 15 may drive more than one gate line GCL collectively.

The signal line selection circuit 16 includes a plurality of selection signal lines Lsel, a plurality of output signal lines Lout, and third switching elements TrS. The third switching elements TrS are provided correspondingly to the signal lines SGL. Six signal lines SGL(1), SGL(2), . . . , SGL(6) are coupled to a common output signal line Lout1. Six signal lines SGL(7), SGL(8), . . . , SGL(12) are coupled to a common output signal line Lout2. The output signal lines Lout1 and Lout2 are each coupled to the detection circuit 48.

The signal lines SGL(1), SGL(2), . . . , SGL(6) are grouped into a first signal line block, and the signal lines SGL(7), SGL(8), . . . , SGL(12) are grouped into a second signal line block. The selection signal lines Lsel are coupled to the gates of the third switching elements TrS included in one of the signal line blocks, respectively. One of the selection signal lines Lsel is coupled to the gates of the third switching elements TrS in the signal line blocks.

The control circuit 102 (refer to FIG. 2) sequentially supplies the selection signal ASW to the selection signal lines Lsel. As a result, through the operations of the third switching elements TrS, the signal line selection circuit 16 sequentially selects the signal lines SGL in one of the signal line blocks in a time-division manner. The signal line selection circuit 16 selects one of the signal lines SGL in each of the signal line blocks. With the above-described configuration, the detection device 1 can reduce the number of integrated circuits (ICs) including the detection circuit 48 or the number of terminals of the ICs. The signal line selection circuit 16 may couple more than one signal line SGL collectively to the detection circuit 48.

As illustrated in FIG. 4, the reset circuit 17 includes a reference signal line Lvr, a reset signal line Lrst, and fourth switching elements TrR. The fourth switching elements TrR are provided corresponding to the signal lines SGL. The reference signal line Lvr is coupled to either the sources or the drains of the fourth switching elements TrR. The reset signal line Lrst is coupled to the gates of the fourth switching elements TrR.

The control circuit 102 supplies a reset signal RST2 to the reset signal line Lrst. This operation turns on the fourth switching elements TrR to electrically couple the signal lines SGL to the reference signal line Lvr. The power supply circuit 103 supplies a reference signal COM to the reference signal line Lvr. This operation supplies the reference signal COM to a capacitive element Ca (refer to FIG. 5) included in each of the partial detection areas PAA.

FIG. 5 is a circuit diagram illustrating the partial detection areas of the first embodiment. FIG. 5 also illustrates a circuit configuration of the detection circuit 48. As illustrated in FIG. 5, each of the partial detection areas PAA includes the photodiode 30, the capacitive element Ca, and a corresponding one of the first switching elements Tr. The capacitive element Ca is a capacitor (sensor capacitor) formed in the photodiode 30, and is equivalently coupled in parallel with the photodiode 30.

FIG. 5 illustrates two gate lines GCL(m) and GCL(m+1) arranged in the second direction Dy of the gate lines GCL. FIG. 5 also illustrates two signal lines SGL(n) and SGL(n+1) arranged in the first direction Dx of the signal lines SGL. The partial detection area PAA is an area surrounded by the gate lines GCL and the signal lines SGL.

Each of the first switching elements Tr is provided corresponding to the photodiode 30. The first switching element Tr includes a thin-film transistor, and in this example, includes an n-channel metal oxide semiconductor (MOS) thin-film transistor (TFT).

The gates of the first switching elements Tr belonging to the partial detection areas PAA arranged in the first direction Dx are coupled to the gate line GCL. The sources of the first switching elements Tr belonging to the partial detection areas PAA arranged in the second direction Dy are coupled to the signal line SGL. The drain of the first switching element Tr is coupled to the cathode of the photodiode 30 and the capacitive element Ca.

The anode of the photodiode 30 is supplied with the sensor power supply signal VDDSNS from the power supply circuit 103. The signal line SGL and the capacitive element Ca are supplied with the reference signal COM that serves as an initial potential of the signal line SGL and the capacitive element Ca from the power supply circuit 103.

When the partial detection area PAA is irradiated with light, a current corresponding to the amount of the light flows through the photodiode 30, and as a result, an electrical charge is stored in the capacitive element Ca. After the first switching element Tr is turned on, a current corresponding to the electrical charge stored in the capacitive element Ca flows through the signal line SGL. The signal line SGL is coupled to the detection circuit 48 through a corresponding one of the third switching elements TrS of the signal line selection circuit 16. Thus, the detection device 1 can detect a signal corresponding to the amount of the light irradiating the photodiode 30 in each of the partial detection areas PAA or in each block unit PAG.

A switch SSW is turned on to couple the detection circuit 48 to the signal lines SGL in a reading period. The detection signal amplifying circuit 42 of the detection circuit 48 converts a variation of a current supplied from the signal lines SGL into a variation of a voltage and amplifies the result. A reference potential (Vref) having a fixed potential is supplied to a non-inverting input portion (+) of the detection signal amplifying circuit 42, and the signal lines SGL are coupled to an inverting input portion (−) of the detection signal amplifying circuit 42. In the embodiment, the same signal as the reference signal COM is supplied as the reference potential (Vref). The signal processing circuit 44 (refer to FIG. 2) calculates the difference between the detection signal Vdet when light is emitted and the detection signal Vdet when light is not emitted, as a sensor output voltage Vo. The detection signal amplifying circuit 42 includes a capacitive element Cb and a reset switch RSW. In a reset period, the reset switch RSW is turned on, and the electrical charge of the capacitive element Cb is reset.

The following describes a configuration of the photodiode 30 and the optical filter 7. FIG. 6 is a sectional view illustrating a schematic sectional configuration of the sensor. As illustrated in FIG. 6, the sensor 10 includes the photodiode (photoelectric conversion element) 30 and a sealing layer 25. The optical filter 7 is provided on the sealing layer 25.

The photodiode 30 includes a detection electrode 31, an electron transport layer 32, an active layer 33, a hole transport layer 34, and a counter electrode 35. The detection electrode 31, the electron transport layer 32, the active layer 33, the hole transport layer 34, and the counter electrode 35 are stacked in this order on the sensor substrate 2.

The detection electrode 31 is electrically coupled to the first switching element Tr (refer to FIG. 5) of the sensor substrate 2 through a contact hole (not illustrated). The detection electrode 31 is the cathode of the photodiode 30 and is an electrode for reading the detection signal Vdet. For example, silver (Ag) or titanium (Ti) is used to fabricate the detection electrode 31. The detection electrode 31 may be made of, for example, a light-transmitting conductive material such as indium tin oxide (ITO).

The electron transport layer 32 and the hole transport layer 34 are provided to facilitate holes and electrons generated in the active layer 33 to reach the counter electrode 35 or the detection electrode 31. For example, zinc oxide (ZnO) and a polythiophene-based conductive polymer (PEDOT:PSS) are used as the electron transport layer 32 and the hole transport layer 34.

The active layer 33 is a thin film made of polyimide having a repeating unit represented by Chemical Formula 6 below. The active layer 33 made of polyimide having a crystalline structure has a photoelectric conversion function. Therefore, when the active layer 33 is irradiated with light, holes and electrons are generated in the active layer 33. The holes and the electrons generated in the active layer 33 move through the electron transport layer 32 and the hole transport layer 34 toward the detection electrode 31 and the counter electrode 35, respectively.

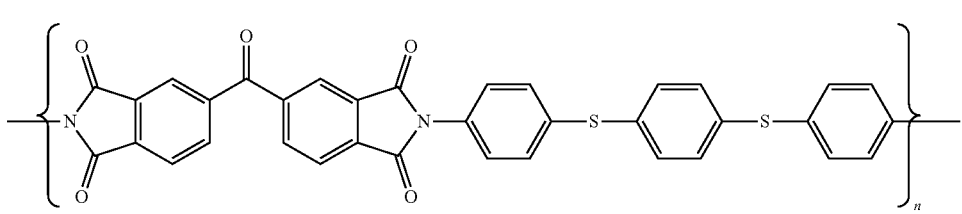

(6)

The counter electrode 35 is the anode of the photodiode 30 and is used to supply the power signal VDDSNS to the active layer 33. The counter electrode 35 faces the detection electrode 31 with the active layer 33 interposed therebetween. The counter electrode 35 is made using ITO, for example.

The sealing layer 25 is a layer for covering the photodiode 30 and planarizing the sensor 10. More specifically, the sealing layer 25 is filled between the photodiodes 30 and covers over the counter electrode 35 of each of the photodiodes 30. The material of the sealing layer 25 is aluminum oxide ($Al_2O_3$).

The optical filter 7 is an optical element that transmits light along the third direction Dz and reduces stray light in directions except the third direction Dz. The optical filter 7 includes a base 70 and a plurality of apertures 71. The base 70 serves as a light-blocking member that does not transmit light. The apertures 71 are cylindrical through-holes formed in the base 70. The base 70 is directly formed on the sealing layer 25. The apertures 71 are arranged along the first direction Dx-second direction Dy plane of the base 70. The optical filter of the present disclosure is not limited to this configuration. The optical filter of the present disclosure may be a multilayer pinhole type formed by alternately laying layers provided with a plurality of holes (pinholes) and transparent resin layers. Alternatively, the optical filter of the present disclosure may be a microlens type in which layers provided with pinholes and transparent resin layers are alternately stacked and microlenses are stacked on the pinholes in a surface on which light is incident.

The following describes a method for manufacturing the photodiode 30. FIG. 7 is a diagram illustrating a manufacturing process of the photodiode according to the first embodiment. FIG. 8 is a diagram illustrating a manufacturing process of the active layer according to the first embodiment. The method for manufacturing the photodiode 30 includes a step S1 of forming the detection electrode 31, a step S2 of forming the electron transport layer 32, a step S3 of forming the active layer 33, a step S4 of forming the hole transport layer 34, and a step S5 of forming the counter electrode 35.

At the step S1, a film of a conductive material such as ITO is formed on the sensor substrate 2 to form the detection electrode 31 using, for example, a vacuum deposition method, a sputtering method, an ion plating method, or a plating method.

At the step S2, a zinc acetate ethanol solution is applied on the detection electrode 31 to form a thin film of zinc acetate sol-gel. Then, the thin film is heated to form the electron transport layer 32 formed of ZnO.

The step S3 of forming the active layer includes a first layer forming step S11, a first heating step S12, and a second heating step S13, as illustrated in FIG. 8. The step S3 of forming the active layer may be referred to as an active layer forming step.

The first layer forming step S11 is a step of applying a solution of polyamic acid serving as a precursor of polyimide on top of the electron transport layer 32 to form a first layer 51.

The first heating step S12 is a step of heating the first layer 51 at 120° C. for 60 minutes. Examples of the heating method include a method of putting the entire sensor substrate 2 into an oven 50 and heating the sensor substrate 2, as illustrated in FIG. 8. The polyamic acid undergoes an imidization reaction by being heated to 200° C. or higher. Therefore, in the first heating step S12, the first layer 51 does not undergo an imidization reaction, and the remaining amount of a solvent decreases, whereby the viscosity is increased.

The second heating step S13 is a step of heating the first layer 51, for example, in the oven 50 at 230° C. to 280° C. for 10 minutes. This second heating step S13 causes the first layer 51 to undergo the imidization reaction and to become the active layer 33. The first heating step S12 and the second heating step S13 of the present disclosure may use a heating means other than the oven 50.

Then, as illustrated in FIG. 7, at the step S4, PEDOT:PSS is applied on the active layer 33, and the active layer 33 is further heated. This step forms the film of the hole transport layer 34.

At the step S5, a film of a conductive material such as ITO or indium zinc oxide (IZO) is formed on the hole transport layer 34 using, for example, the vacuum deposition method, the sputtering method, the ion plating method, or the plating method, whereby the counter electrode 35 is formed.

As described above, the photodiode (photoelectric conversion element) 30 manufactured by the manufacturing method of the first embodiment has higher crystallinity than conventional ones and excels in sensitivity in photoelectric conversion. The active layer 33 is made of polyimide and does not thermally deteriorate up to 320° C. In the case of the active layer having a bulk hetero structure in which phenyl-C61-butyric acid methyl ester (PCBM) is mixed with poly (3-hexylthiophene) (P3HT) and F8-alt-benzothiadiazole (F8BT), the heat resisting temperature is 100° C. Therefore, the photodiode (photoelectric conversion element) 30 manufactured by the manufacturing method of the first embodiment has a higher heat resisting temperature than conventional ones. Thus, conventionally, when the optical filter 7 is formed on the sealing layer 25 covering the photodiode 30, the active layer 33 may be thermally affected, and the optical filter 7 is separately manufactured and adhesively bonded onto the sensor 10 using adhesive tape. However, according to the active layer 33 of the first embodiment, even if the optical filter 7 is directly formed on top of the sealing layer 25 by, for example, a photolithography process, the effect given to the active layer 33 is low. That is, the present embodiment eliminates the need for providing the adhesive tape for adhesively bonding the optical filter 7, and the detection device 1 thereby is made thinner.

While the photoelectric conversion element according to the first embodiment has been described above, the photoelectric conversion element of the present disclosure is not limited to that described above. Other embodiments will be described below, mainly focusing on differences from the photoelectric conversion element according to the first embodiment.

Second Embodiment

FIG. 9 is a sectional view illustrating a schematic sectional configuration of a sensor according to a second embodiment of the present disclosure. A photodiode 30A according to the second embodiment differs from the photodiode 30 according to the first embodiment in including an active layer 33A instead of the active layer 33.

The active layer 33A according to the second embodiment is a thin film formed of polyimide having a repeating unit represented by Chemical Formula 7 below. The active layer 33A has a crystalline structure and has a photoelectric conversion function.

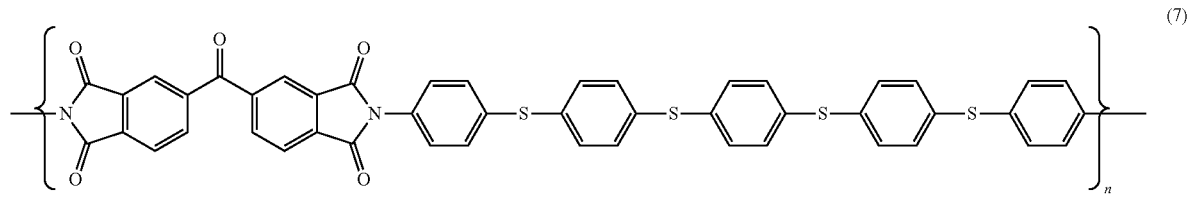

(7)

FIG. 10 is a diagram illustrating a manufacturing process of the active layer according to the second embodiment. In the same manner as in the first embodiment, the method for manufacturing the photodiode 30A includes the step S1 of forming the detection electrode 31, the step S2 of forming the electron transport layer 32, the step S3 of forming the active layer 33A, the step S4 of forming the hole transport layer 34, and the step S5 of forming the counter electrode 35 (refer to FIG. 7). The step of forming the active layer 33A includes a first layer forming step S21, a first heating step S22, and a second heating step S23, as illustrated in FIG. 10.

Third Embodiment

FIG. 11 is a sectional view illustrating a schematic sectional configuration of a sensor according to a third embodiment of the present disclosure. A photodiode 30B according to the third embodiment differs from the photodiode 30 according to the first embodiment in including an active layer 33B instead of the active layer 33.

The active layer 33B according to the third embodiment is a thin film formed of polyimide having a repeating unit represented by Chemical Formula 8 below. The active layer 33B has a crystalline structure and has a

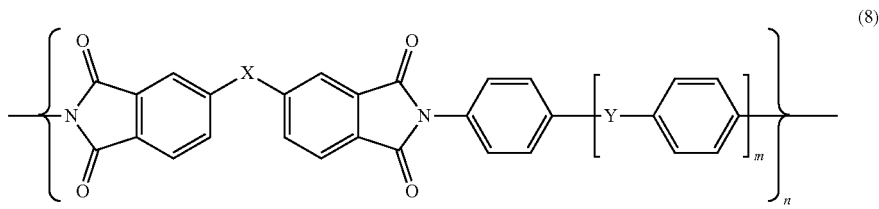

(8)

At the first layer forming step S21, a first layer 52 is formed by applying a polyamic acid solution serving as a precursor on top of the electron transport layer 32.

The first heating step S22 is a step of putting the entire sensor substrate 2 into the oven 50 and heating the first layer 52 at 120° C. for 20 minutes to 80 minutes. The polyamic acid (precursor) undergoes an imidization reaction by being heated at 200° C. or higher. Therefore, at the first heating step S22, the first layer 52 does not undergo the imidization reaction, and the remaining amount of the solvent decreases.

The second heating step S23 is a step of heating the first layer 52 in the oven 50 at 180° C. to 260° C. for 10 minutes. Through this step, the polyamic acid (precursor) in the first layer 52 undergoes the imidization reaction, and the active layer 33A is formed.

The manufacturing method of the second embodiment can also produce the photodiode 30 having the active layer 33A of high crystallinity and being excellent in sensitivity in photoelectric conversion. The heat resisting temperature of the active layer 33A is as high as 300° C. or higher. The optical filter 7 can be directly formed on top of the sealing layer 25, and the detection device 1 can be made thinner.

X: —O—, —S—, >CO, >C—$R_2$, >$SO_2$, —C(=O)—O—, —C(=O)—O-ϕ-O—C(=O)— where R: —H, —$CH_3$, —$CF_3$,

Y: S, Se, Te, m: 2, 4, 6, 8, 10, and n: three or more oligomers or polymers

FIG. 12 is a diagram illustrating a manufacturing process of the active layer according to the third embodiment. In the same manner as in the first embodiment, the method for manufacturing the photodiode 30B includes the step S1 of forming the detection electrode 31, the step S2 of forming the electron transport layer 32, the step S3 of forming the active layer 33B, the step S4 of forming the hole transport layer 34, and the step S5 of forming the counter electrode 35 (refer to FIG. 7). The step of forming the active layer 33B includes a first layer forming step S31, a first heating step S32, and a second heating step S33, as illustrated in FIG. 12.

The first layer forming step S31 is a step of applying polyamide acid serving as a precursor on top of the electron transport layer 32 to form a first layer 53. The polyamide acid has a repeating unit represented by Chemical Formula 9 below. The polyamide acid of the following formula is obtained by a dehydration condensation reaction between an acid anhydride and a diamine compound.

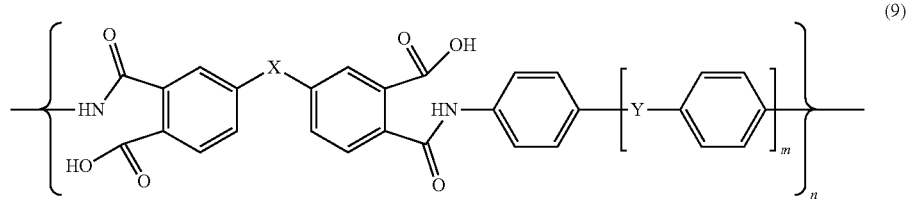

(9)

X: —O—, —S—, >CO, >C—R$_2$, >SO$_2$, —C(=O)—O—, —C(=O)—O-φ-O—C(=O)— where R: —H, —CH$_3$, —CF$_3$,

Y: S, Se, Te, m: 2, 4, 6, 8, 10, and n: three or more oligomers or polymers

The first heating step S32 is a step to put the first layer 53 into the oven 50 and heat the first layer 53 at 120° C. for 20 minutes. The polyamide acid of the above formula undergoes an imidization reaction by being heated at 200° C. or higher. Therefore, in the first heating step S32, the first layer 53 does not undergo the imidization reaction.

The second heating step S33 is a step of heating the first layer 53 in the oven 50 at 200° C. to 240° C. for 10 minutes. Through this step, the polyamide acid in the first layer 53 undergoes an imidization reaction and the active layer 33B is formed.

As described above, the manufacturing method of the third embodiment can also produce the photodiode 30B having the active layer 33B of high crystallinity and being excellent in sensitivity in photoelectric conversion. The heat resisting temperature of the active layer 33B is as high as 300° C., and the optical filter 7 can be directly formed on top of the sealing layer 25 (sensor 10). Therefore, the detection device 1 can be made thinner.

Fourth Embodiment

FIG. 13 is a sectional view illustrating a schematic sectional configuration of a sensor according to a fourth embodiment of the present disclosure. A photodiode 30C according to the fourth embodiment differs from the photodiode 30 according to the first embodiment in including an active layer 33C instead of the active layer 33.

The active layer 33C of the fourth embodiment is formed of a heterojunction of an n-type semiconductor 38 and a p-type semiconductor 37. The p-type semiconductor 37 is one of the polyimides represented by Chemical Formulae 5, 6, and 7 described in the first to the third embodiments and has a crystalline structure. Therefore, the p-type semiconductor 37 alone has a photoelectric conversion function.

The n-type semiconductor 38 is obtained by heat-treating and crystallizing a soluble porphyrin or a phthalocyanine compound. The n-type semiconductor 38 has a plurality of column-like pillar portions 38a extending toward the hole transport layer 34, and a three-dimensional p-n junction is formed with the n-type semiconductor 38 and the p-type semiconductor 37. Therefore, a large amount of current can be extracted from an interface between the n-type semiconductor 38 and the p-type semiconductor 37. Therefore, the sensitivity of the photoelectric effect is higher in the active layer 33C than in a single layer of the p-type semiconductor 37, in other words, than in the active layers 33, 33A, and 33B of the first to the third embodiments. The following describes a manufacturing method of the active layer 33C of the fourth embodiment.

FIG. 14 is a diagram illustrating a manufacturing process of the active layer according to the fourth embodiment. The step of forming the active layer 33C includes a base layer forming step S41, a base layer heating step S42, a first layer forming step S43, a first heating step S44, and a second heating step S45, as illustrated in FIG. 14.

The base layer forming step S41 is a step of applying a soluble porphyrin or a phthalocyanine compound on top of the electron transport layer 32 to form a base layer 54.

The base layer heating step S42 is a step of heating the base layer 54 in the oven 50 at 150° C. for 30 minutes. This step cures the base layer 54 to be a portion of the n-type semiconductor 38.

The first layer forming step S43 is a step at which a mixture of one of the polyimides represented by Chemical Formulae 5, 6, and 7 and the soluble porphyrin or the phthalocyanine compound used in the base layer 54 is applied on top of a portion of the n-type semiconductor 38 to form a first layer 55.

At the first heating step S44, the entire sensor substrate 2 is put in the oven 50 and the first layer 55 is heated at 120° C. for 60 minutes.

Then, at the second heating step S45, the first layer 55 is heated at 120° C. to 180° C. for 10 minutes. This step forms the soluble porphyrin or the phthalocyanine compound contained in the first layer 55 into the pillar portions 38a extending toward the hole transport layer 34 (refer to FIG. 13) using the n-type semiconductor 38 as a base material, as illustrated in FIG. 14. The polyimide also undergoes the imidization reaction, thereby forming the crystallized p-type semiconductor 37.

FIG. 15 is a sectional view illustrating a modification of the active layer of the fourth embodiment. In the present disclosure, the soluble porphyrin or the phthalocyanine compound in the first layer 55 of the active layer 33C in the heterojunction state need not be formed into a column-like shape at the second heating step S45. For example, as illustrated in FIG. 15, the n-type semiconductor 38 may be mixed with the p-type semiconductor 37.

As described above, the manufacturing method of the fourth embodiment can produce a photodiode 30C (photoelectric conversion element) having further improved sensitivity of the photoelectric effect.

FIG. 16 is a sectional view illustrating a modification of the photoelectric conversion element. While the embodiments have been described above, the photodiode (photoelectric conversion element) of the present disclosure may be a photodiode 30D in which the stacking order of the detection electrode 31, the electron transport layer 32, the active layer 33, the hole transport layer 34, and the counter electrode 35 is reversed from that described in the first to the fourth embodiments, as illustrated in FIG. 16.

EXAMPLES

The following describes examples. In a first example, photodiodes (photoelectric conversion elements) were produced using the manufacturing method of the first embodiment, and the crystallinity of the photodiodes was checked. In a second example, photodiodes (photoelectric conversion elements) were produced using the manufacturing method of the second embodiment, and the crystallinity of the photodiodes was checked. The following describes the first and the second examples.

First Example

FIG. 17 is a chart illustrating X-ray diffraction analysis results of Samples 1 to 8. FIG. 18 is a graph illustrating a relation between a full width at half maximum of an X-ray spectrum and the substrate temperature at the time of film formation in Samples 2, 3, 4, 5, 6, 7, and 8. In Example 1, a total of eight photodiodes (hereinafter referred to as Sample 1, Sample 2, . . . , Sample 8) were manufactured. Some of the samples were produced by the manufacturing method of the first embodiment, and the rest were produced by manufacturing methods (comparative examples) other than the manufacturing method of the first embodiment.

To describe it in detail, for Samples 1 to 8, the first layer 51 was formed using a first liquid composed of a polyamic acid at the first layer forming step S11. For Samples 1 to 6, the first layer 51 was heated at 120° C. for 60 minutes at the first heating step S12. Samples 7 and 8 were not subjected to the first heating step S12. Therefore, Samples 7 and 8 are comparative examples.

At the second heating step S13, the heating temperature and time were changed between Samples 1 to 8. Specifically, Sample 1 was heated at 120° C. for 20 to 60 minutes. Sample 2 was heated at 200° C. for 10 minutes. Sample 3 was heated at 220° C. for 10 minutes. Sample 4 was heated at 240° C. for 10 minutes. Sample 5 was heated at 260° C. for 10 minutes. Sample 6 was heated at 280° C. for 10 minutes. Sample 7 was heated at 280° C. for 60 minutes. Sample 8 was heated at 290° C. for 60 minutes. Thus, Samples 1, 2, 3, 7, and 8 are comparative examples that do not satisfy the condition of heating at 230° C. to 280° C. for 10 minutes specified in the embodiments.

Then, using an X-ray diffractometer, the crystallinity of Samples 1 to 8 was analyzed. FIG. 17 illustrates the results of the analysis.

As illustrated in FIG. 17, no clear peak was found in Samples 1 to 3, and 7. That is, it has been found that the polyimide (active layer 33) in the Samples 1 to 3, and 7 is mainly placed in an amorphous state without being crystallized at the second heating step S13. Clear diffraction peaks were found at 2θ=18.5° and 2θ=22.3° in Samples 4 to 6. Diffraction peak values were also high. Thus, it has been found that the polyimide (active layer 33) is sufficiently crystallized. In Sample 8, although a diffraction peak was present at 2θ=22.3°, the peak value was small, and the crystallinity was not sufficient.

Then, for each of Samples 2, 3, 4, 5, 6, 7, and 8, the full width at half maximum of the X-ray spectrum during the X-ray diffraction (2θ=18.5° for samples 2, 3, 4, 5, and 6, and 2θ=22.3° for samples 7 and 8) was obtained, and the size of a crystallite was obtained. In the same manner as Sample 7, Sample 8 is a photodiode formed without undergoing the first heating step S12, and the heating temperature of the second heating step S13 is 280° C. and 290° C. FIG. 18 illustrates the full width at half maximum of the X-ray spectrum.

As illustrated in FIG. 18, the full width at half maximum decreased in the order of Sample 2, Sample 3, Sample 4, Sample 5, and Sample 6. Therefore, it has been found that, in the range where the heating temperature of the second heating step is from 200° C. to 260° C., the size of the crystallites increases and the crystallinity improves as the heating temperature increases. The values of the full width at half maximum of the Samples 7 and 8 were equal to or higher than 0.7, resulting in high polycrystallinity. Thus, a result has been obtained that Samples 4, 5, and 6 heated at the second heating step S13 at heating temperature of 230° C. to 280° C. have higher crystallinity and more excellent sensitivity of the photoelectric conversion than Samples 7 and 8 do.

Second Example

FIG. 19 is a chart illustrating X-ray diffraction analysis results of Samples 11 to 16. FIG. 20 is a graph illustrating a relation between the full width at half maximum of the X-ray spectrum and the substrate temperature at the time of film formation in Samples 11 to 16 according to the second example. The following describes the second example. In the second example, a total of six photodiodes (hereinafter referred to as Sample 11, Sample 12, . . . , Sample 16) were produced. Some of the samples were produced by the manufacturing method of the second embodiment, and the rest were produced by manufacturing methods (comparative examples) other than the manufacturing method of the second embodiment.

To describe it in detail, for Samples 11 to 16, the first layer 52 was formed by applying an amic acid solution serving as a precursor of Chemical Formula 2 at the first layer forming step S21. For samples 11 to 16, the first layer 52 was heated at 120° C. for 20 to 60 minutes at the first heating step S12.

At the second heating step S13, the heating temperature was changed between Samples 11 to 16. Specifically, Sample 11 was heated at 180° C. Sample 12 was heated at 200° C. Sample 13 was heated at 220° C. Sample 14 was heated at 240° C. Sample 15 was heated at 260° C. Sample 16 was heated at 280° C. Thus, Samples 11 to 15 satisfy the condition of heating at 180° C. to 260° C. for 10 minutes specified in the second embodiment, and only Sample 16 is a comparative example that does not satisfy the condition specified in the embodiment. The heating time was set to 10 minutes for all Samples 11 to 16.

Then, using the X-ray diffractometer, the crystallinity of Samples 11 to 16 was analyzed. FIG. 19 illustrates the results of the analysis. The full width at half maximum of the X-ray spectrum during the X-ray diffraction (2θ=18.6° and 2θ=22.0°) was obtained, and the size of the crystallite was obtained. FIG. 20 illustrates the full width at half maximum of the X-ray spectrum.

As illustrated in FIG. 19, diffraction peaks were found at 2θ=18.6° and 2θ=22.0° in Samples 11 to 16. For Samples 11 to 15, diffraction peak values were also high, and the polyimide film was sufficiently crystallized. For Sample 16, the peak value was small, and the crystallinity was not sufficient. Therefore, it has been found that the polyimide film are sufficiently crystallized when the condition of heating at 180° C. to 260° C. for 10 minutes is satisfied at the second heating step S23.

As illustrated in FIG. 20, Sample 13 (with heating temperature of 220° C.) among Samples 11 to 15 exhibited the value of the full width at half maximum equal to or smaller than 0.4, and exhibited a high degree of crystal unity. Therefore, it has been found that Sample 13 has the highest crystallinity and the excellent sensitivity of the photoelectric conversion among Samples 11 to 15.

What is claimed is:

1. A method for manufacturing a photoelectric conversion element, the method comprising an active layer forming step of forming an active layer having a repeating unit represented by Chemical Formula 1 below, wherein
   the active layer forming step comprises:
   a first layer forming step of forming a first layer by applying polyamic acid serving as a precursor;
   a first heating step of heating the first layer at 120° C. for 20 minutes to 60 minutes; and a second heating step of heating the first layer at 230° C. to 280° C. for 10 minutes,

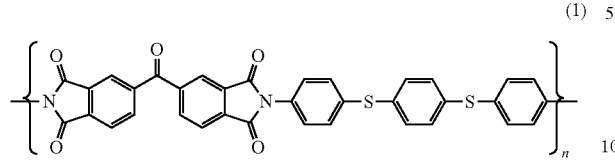

n: a natural number of >2.

2. The method for manufacturing a photoelectric conversion element according to claim 1, the method further comprising:
a base layer forming step of forming a base layer of the active layer by applying a soluble porphyrin or a phthalocyanine compound; and
a base layer heating step of heat-treating the base layer at 150° C., wherein
in the first layer forming step, the first layer is formed by applying a mixture obtained by adding the soluble porphyrin or the phthalocyanine compound used for the base layer to the precursor after the base layer heating step.

3. A method for manufacturing a photoelectric conversion element, the method comprising an active layer forming step of forming an active layer having a repeating unit represented by Chemical Formula 2 below, wherein
the active layer forming step comprises:
a first layer forming step of forming a first layer by applying a polyamic acid solution serving as a precursor of Chemical Formula 2 below;
a first heating step of heating the first layer at 120° C. for 20 minutes to 60 minutes; and
a second heating step of heating the first layer at 180° C. to 280° C. for 10 minutes,

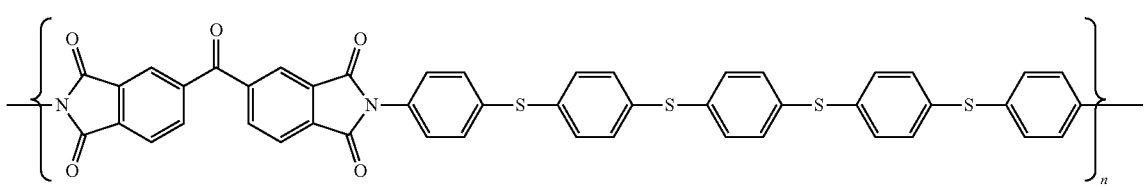

n: a natural number of >2.

4. The method for manufacturing a photoelectric conversion element according to claim 3, the method further comprising:
a base layer forming step of forming a base layer of the active layer by applying a soluble porphyrin or a phthalocyanine compound; and
a base layer heating step of heat-treating the base layer at 150° C., wherein
in the first layer forming step, the first layer is formed by applying a mixture obtained by adding the soluble porphyrin or the phthalocyanine compound used for the base layer to the precursor after the base layer heating step.

5. A method for manufacturing a photoelectric conversion element, the method comprising an active layer forming step of forming an active layer having a repeating unit represented by Chemical Formula 3 below, wherein
the active layer forming step comprises:
a first layer forming step of forming a first layer by applying polyamide acid that serves as a precursor and has a repeating unit represented by Chemical Formula 4 below;
a first heating step of heating the first layer at 120° C. for 20 minutes to 60 minutes; and
a second heating step of heating the first layer at 180° C. to 280° C. for 10 minutes,

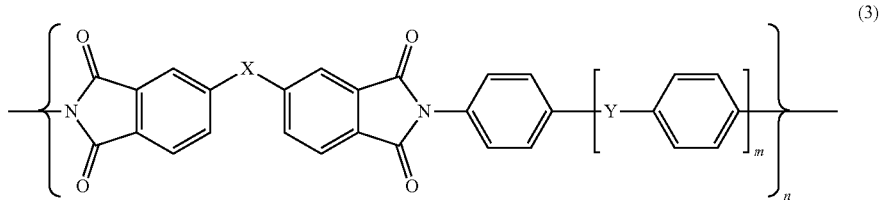

X: —O—, —S—, >CO, >C—R$_2$, >SO$_2$, —C(=O)—O—, —C(=O)—O-φ-O—C(=O)— where R: —H, —CH$_3$, —CF$_3$,

Y: S, Se, Te, m: 2, 4, 6, 8, 10, and n: three or more oligomers or polymers

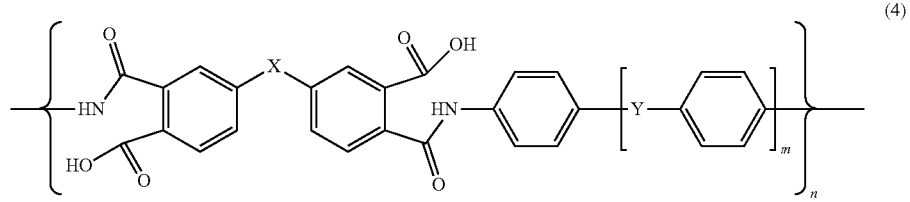

(4)

X: —O—, —S—, >CO, >C—R$_2$, >SO$_2$, —C(=O)—O—, —C(=O)—O-φ-O—C(=O)— where R: —H, —CH$_3$, —CF$_3$,

Y: S, Se, Te, m: 2, 4, 6, 8, 10, and n: three or more oligomers or polymers.

6. The method for manufacturing a photoelectric conversion element according to claim 5, the method further comprising:

a base layer forming step of forming a base layer of the active layer by applying a soluble porphyrin or a phthalocyanine compound; and a base layer heating step of heat-treating the base layer at 150° C., wherein in the first layer forming step, the first layer is formed by applying a mixture obtained by adding the soluble porphyrin or the phthalocyanine compound used for the base layer to the precursor after the base layer heating step.

* * * * *